(12) United States Patent
Ou et al.

(10) Patent No.: US 11,712,229 B2
(45) Date of Patent: Aug. 1, 2023

(54) SYSTEMS, DEVICES AND METHODS FOR DISPENSING AND CURING SILICONE BASED TOPICAL SKIN ADHESIVES

(71) Applicant: Ethicon, Inc., Somerville, NJ (US)

(72) Inventors: Duan Li Ou, Watchung, NJ (US); Frank Richard Cichocki, Jr., Easton, PA (US); Glenn R. Cook, Clinton, NJ (US)

(73) Assignee: Ethicon, Inc., Raritan, NJ (US)

( * ) Notice: Subject to any disclaimer, the term of this patent is extended or adjusted under 35 U.S.C. 154(b) by 328 days.

(21) Appl. No.: 16/885,413

(22) Filed: May 28, 2020

(65) Prior Publication Data
US 2021/0369258 A1    Dec. 2, 2021

(51) Int. Cl.
  *A61B 17/00*    (2006.01)
  *A61M 5/19*    (2006.01)

(52) U.S. Cl.
  CPC .. *A61B 17/00491* (2013.01); *A61B 2017/005* (2013.01); *A61B 2017/00495* (2013.01); *A61M 5/19* (2013.01)

(58) Field of Classification Search
  CPC .... A61B 17/00491; A61B 2017/00495; A61B 2017/005; A61M 5/19; A61M 35/003; B05C 17/00553; B05C 17/00509; B05C 17/00516; B05C 17/0052
  See application file for complete search history.

(56) References Cited

U.S. PATENT DOCUMENTS

| | | | |
|---|---|---|---|
| 2,941,696 A | 6/1960 | Edwin |
| 3,187,752 A | 6/1965 | Glick |
| 3,445,420 A | 5/1969 | Kookootsedes et al. |
| 3,490,651 A | 1/1970 | Abplanalp |
| 3,675,821 A | 7/1972 | Morane et al. |
| 3,775,452 A | 11/1973 | Karstedt |

(Continued)

FOREIGN PATENT DOCUMENTS

| | | |
|---|---|---|
| CN | 104531056 A | 4/2015 |
| CN | 105586001 A | 5/2016 |

(Continued)

OTHER PUBLICATIONS

Google scholar keyword search (Year: 2021), 2 sheets.

(Continued)

*Primary Examiner* — Mohamed G Gabr

(57) ABSTRACT

A system for dispensing a curable composition includes a dual barrel syringe including a first syringe barrel with a first plunger, and a second syringe barrel with a second plunger. A static mixer is connected with distal ends of the first and second syringe barrels. The first and second plungers are moveable toward the distal ends of the first and second syringe barrels for expelling first and second components of a curable composition from the distal ends of the barrels into the static mixer for mixing the components to form the curable composition. A flexible spreader connected with a distal end of the static mixer has a flat dispensing opening, and a plurality of channels extending to the flat dispensing opening to dispense the curable composition. A hot gas blower generates a hot gas stream flowing distally over the distal end of the flexible spreader for curing the curable composition.

17 Claims, 18 Drawing Sheets

(56) References Cited

U.S. PATENT DOCUMENTS

| | | | |
|---|---|---|---|
| 3,814,730 A | 6/1974 | Karstedt | |
| 4,234,108 A | 11/1980 | Diamond | |
| 4,340,155 A | 7/1982 | Obrist | |
| 4,791,149 A | 12/1988 | Pocknell | |
| 5,020,694 A | 6/1991 | Pettengill | |
| 5,026,768 A | 6/1991 | Liles | |
| 5,211,316 A | 5/1993 | Adalberto et al. | |
| 5,431,303 A | 7/1995 | Miskell | |
| 5,447,987 A | 9/1995 | Sato et al. | |
| 5,577,637 A | 11/1996 | Voss | |
| 5,647,510 A | 7/1997 | Keller | |
| 5,776,268 A | 7/1998 | Mcjames et al. | |
| 5,780,543 A | 7/1998 | Adachi et al. | |
| 6,265,480 B1 | 7/2001 | Enami et al. | |
| 6,537,246 B1 | 3/2003 | Unger et al. | |
| 6,613,185 B1 | 9/2003 | Valade et al. | |
| 6,951,654 B2 | 10/2005 | Malcolm et al. | |
| 7,393,547 B2 | 7/2008 | Nelson | |
| 7,481,333 B2 | 1/2009 | Goldberg et al. | |
| 7,798,366 B2 | 9/2010 | Hoshino | |
| 8,021,650 B2 | 9/2011 | Tamareselvy et al. | |
| 8,357,147 B2 | 1/2013 | Burkinshaw et al. | |
| 8,430,588 B2 * | 4/2013 | Haack | B05C 5/027 401/5 |
| 8,596,499 B2 | 12/2013 | Vogt et al. | |
| 8,728,599 B2 | 5/2014 | Fang et al. | |
| 8,969,910 B2 | 3/2015 | Katayama | |
| 9,038,858 B2 | 5/2015 | Hanai et al. | |
| 9,180,476 B2 | 11/2015 | Werner et al. | |
| 9,302,282 B2 | 4/2016 | Bertin et al. | |
| 9,408,971 B2 | 8/2016 | Carlyon | |
| 9,422,404 B2 | 8/2016 | Curtis et al. | |
| 9,434,857 B2 | 9/2016 | Ou | |
| 9,511,034 B1 | 12/2016 | Garrett | |
| 9,642,949 B2 | 5/2017 | Hai et al. | |
| 9,649,650 B2 | 5/2017 | Werner et al. | |
| 9,655,917 B2 | 5/2017 | Hai et al. | |
| 9,764,099 B2 | 9/2017 | Rimsa et al. | |
| 10,219,793 B2 | 3/2019 | Quintero et al. | |
| 10,441,947 B2 | 10/2019 | Ou | |
| 2001/0011162 A1* | 8/2001 | Epstein | A61M 1/7413 604/35 |
| 2001/0019721 A1 | 9/2001 | Brandt et al. | |
| 2002/0076260 A1 | 6/2002 | Heusser | |
| 2002/0193879 A1 | 12/2002 | Seder et al. | |
| 2003/0044451 A1 | 3/2003 | Mcghee et al. | |
| 2003/0050597 A1* | 3/2003 | Dodge | A61B 17/00491 604/82 |
| 2003/0077316 A1 | 4/2003 | Nichols et al. | |
| 2003/0082223 A1 | 5/2003 | Healy et al. | |
| 2003/0183651 A1 | 10/2003 | Greer | |
| 2004/0004088 A1 | 1/2004 | Yerby et al. | |
| 2004/0181943 A1 | 9/2004 | Kwiecien | |
| 2005/0020844 A1 | 1/2005 | Nelson | |
| 2005/0029296 A1 | 2/2005 | Hansen et al. | |
| 2005/0048124 A1 | 3/2005 | Sarangapani | |
| 2005/0127119 A1 | 6/2005 | Keller | |
| 2005/0182443 A1 | 8/2005 | Jonn et al. | |
| 2005/0256573 A1 | 11/2005 | Seder et al. | |
| 2006/0009099 A1 | 1/2006 | Jonn et al. | |
| 2006/0134313 A1 | 6/2006 | Guggenbichler et al. | |
| 2007/0043332 A1 | 2/2007 | Malcolm et al. | |
| 2007/0104665 A1 | 5/2007 | Jones et al. | |
| 2007/0293820 A1 | 12/2007 | Dacquay | |
| 2008/0054020 A1 | 3/2008 | Pierson et al. | |
| 2008/0275403 A1 | 11/2008 | Maaskamp et al. | |
| 2009/0004246 A1 | 1/2009 | Woolfson et al. | |
| 2009/0026660 A1 | 1/2009 | Nelson et al. | |
| 2009/0076480 A1 | 3/2009 | Pudleiner et al. | |
| 2009/0108021 A1 | 4/2009 | Hansen et al. | |
| 2010/0280547 A1 | 11/2010 | D'Alessio et al. | |
| 2010/0330025 A1 | 12/2010 | Messersmith et al. | |
| 2011/0027753 A1* | 2/2011 | Maurat | A61C 9/0026 433/141 |
| 2011/0091669 A1 | 4/2011 | Tang et al. | |
| 2011/0143148 A1 | 6/2011 | Butts et al. | |
| 2011/0272433 A1 | 11/2011 | Vogt et al. | |
| 2012/0237461 A1 | 9/2012 | Yu et al. | |
| 2012/0328787 A1 | 12/2012 | Marrot et al. | |
| 2013/0004586 A1* | 1/2013 | Vachon | B01J 41/07 424/641 |
| 2013/0059109 A1 | 3/2013 | Kretschmann et al. | |
| 2013/0122314 A1 | 5/2013 | Ou | |
| 2013/0123720 A1 | 5/2013 | Lind et al. | |
| 2013/0150828 A1 | 6/2013 | Conway | |
| 2013/0171265 A1 | 7/2013 | Saxena et al. | |
| 2013/0310780 A1 | 11/2013 | Phillips | |
| 2013/0310781 A1 | 11/2013 | Phillips et al. | |
| 2014/0221522 A1 | 8/2014 | Antoni et al. | |
| 2015/0159066 A1 | 6/2015 | Hartwell et al. | |
| 2016/0120706 A1 | 5/2016 | Collinson et al. | |
| 2016/0220497 A1 | 8/2016 | Caprasse et al. | |
| 2016/0354172 A1 | 12/2016 | Krogman et al. | |
| 2017/0224823 A1 | 8/2017 | Blanda et al. | |
| 2018/0030327 A1 | 2/2018 | Zhang et al. | |
| 2018/0163090 A1 | 6/2018 | Ou | |
| 2018/0338945 A1 | 11/2018 | Sambasivam | |
| 2019/0001019 A1 | 1/2019 | Lindgren et al. | |
| 2020/0172740 A1 | 6/2020 | Ou et al. | |
| 2021/0369258 A1 | 12/2021 | Ou et al. | |
| 2021/0369276 A1 | 12/2021 | Ou et al. | |
| 2021/0369639 A1 | 12/2021 | Ou | |
| 2021/0371190 A1 | 12/2021 | Ou et al. | |
| 2021/0371596 A1 | 12/2021 | Ou et al. | |
| 2021/0371658 A1 | 12/2021 | Ou | |
| 2021/0371662 A1 | 12/2021 | Ou | |

FOREIGN PATENT DOCUMENTS

| | | |
|---|---|---|
| CN | 106009688 A | 10/2016 |
| EP | 3388037 A1 | 10/2018 |
| JP | 11349897 A | 12/1999 |
| KR | 2016-0039498 A | 4/2016 |
| WO | 9725085 A1 | 7/1997 |
| WO | 2010128855 | 11/2010 |
| WO | 2013/074732 A1 | 5/2013 |
| WO | 2016094084 A1 | 6/2016 |
| WO | 2017158340 A1 | 9/2017 |

OTHER PUBLICATIONS

International Search Report dated Aug. 13, 2021 for International Application No. PCT/IB2021/054533, 6 sheets.
International Search Report dated Aug. 18, 2021 for International Application No. PCT/IB2021/054531, 6 sheets.
International Search Report dated Feb. 21, 2020 for International Application No. PCT/IB2019/060233, 7 sheets.
International Search Report dated Feb. 21, 2020 for International Application No. PCT/IB2019/060235, 7 sheets.
International Search Report dated Jan. 11, 2022 for International Application No. PCT/IB2021/054534, 7 sheets.
International Search Report dated Jul. 29, 2021 for International Application No. PCT/IB2021/054515, 6 sheets.
International Search Report dated Jul. 30, 2021 for International Application No. PCT/IB2021/054518, 6 sheets.
IP.com search of the PGPub (Year: 2021), 1 sheet.
Lewis, et al., "The chemistry of fumarate and maleate inhibitors with platinum hydrosilylation catalysts", Journal of Organometallic Chemistry, 1996, vol. 521, pp. 221-227.
XP002797679, Database WPI, 2016, Thomson Scientific, London, GB; AN 2016-25340X; 2 sheets.
XP002797623, Database WPI, 2015, Thomson Scientific, London, GB; AN 2015-37318P; 2 sheets.
XP002797624, Database WPI, 2017, Thomson Scientific, London, GB; AN 2016-67448B; 2 sheets.
XP002797604, Database WPI, 2016, Thomson Scientific, London, GB; AN 2016-25340X; 2 sheets.
XP002797605, Database WPI, 2016, Thomson Scientific, London, GB; AN 2015-37318P; 2 sheets.

(56) References Cited

OTHER PUBLICATIONS

XP002797606, Database WPI, 2017, Thomson Scientific, London, GB; AN 2016-67448B; 2 sheets.

* cited by examiner

SYSTEMS, DEVICES AND METHODS FOR DISPENSING AND CURING SILICONE BASED TOPICAL SKIN ADHESIVES

CROSS-REFERENCE TO RELATED APPLICATIONS

Field of the Invention

The present patent application is related to the following commonly assigned United States patent applications, which were all filed on May 28, 2020: U.S. patent application Ser. No. 16/885,426, U.S. patent application Ser. No. 16/885,361, U.S. patent application Ser. No. 16/885,366, and U.S. patent application Ser. No. 16/885,375. The disclosures of all of the above-identified United States patent applications are hereby incorporated by reference herein.

BACKGROUND OF THE INVENTION

Field of the Invention

The present patent application is generally related to medical devices for dispensing compositions, and is more specifically related to systems, devices and methods for dispensing, applying, and curing topical skin adhesives used to close wounds.

Description of the Related Art

There are many different methods and techniques used to close wounds that result from surgical incisions and accidental lacerations. These methods and techniques include using sutures, using surgical staples, using surgical skin tapes, and using topical skin adhesives that are applied directly to a skin surface.

Sutures are generally recognized as providing adequate wound support for the duration of wound healing, however, suturing involves additional trauma to the wound because a needle and suture material must pass through the tissue at the margins of the wound. Suturing can also cause cosmetically unattractive wound closure marks and can be time consuming. In addition, depending on the techniques and types of sutures that are used, the sutures may need to be removed at a later date, which could require further medical attention and cause more pain and trauma for a patient In terms of cosmetic results, surgical staples can have many of the same disadvantages as those described above for sutures. Moreover, removing surgical staples can be painful and, depending upon the location and the patient's pain threshold, may require the use of topical anesthesia. Recently, absorbable surgical staples have been developed that are absorbed by the patient's body over time and do not have to be removed.

Skin closure strips, such as conventional adhesive bandages, are typically utilized for closing relatively superficial skin wounds, however, their use is limited to only certain types and degrees of wounds. The contact adhesives that are used with skin closure strips typically retain holding power for no more than a day or two and can lose holding power quickly in the presence of moisture (e.g., perspiration).

The direct application of adhesives to tissue and skin has also been used for wound closure purposes. For example, monomer and polymer adhesives can be used in medical applications. Since their initial discovery, monomer and polymer adhesives have been widely adopted for various medical applications due to the speed with which they cure, the strength of the resulting bond that is formed, and their relative ease of use. One widely used topical skin adhesive product is sold under the trademark DERMABOND® by Johnson & Johnson Corporation of New Brunswick, N.J.

Adhesives used for medical procedures are typically stored in deformable containers or tubes. Deformable tubes are usually made of metals or plastics that are squeezable for dispensing the adhesive. Squeezing a metal or plastic tube by hand expresses the substance contained in the tube through a delivery nozzle, which can be a tricky and messy operation, especially when the tube is not completely full. Moreover, the amount of adhesive substance being expressed is not easy to regulate by pressing with fingers, and it is difficult to simultaneously regulate the amount that is dispensed while the adhesive is being applied to a substrate.

In order to overcome the above-identified problems, there have been some activities directed to developing delivery devices for dispensing topical skin adhesives. For example, U.S. Pat. No. 10,219,793, assigned to Ethicon, Inc. of Somerville, N.J., discloses a delivery system including a squeezable container that contains a topical skin adhesive and a container support frame that holds the squeezable container. The container support frame includes a proximal edge secured to a sealed proximal end of the squeezable container, a distal edge secured to a dispensing neck of the squeezable container, and first and second lateral edges extending between the proximal and distal edges and overlying opposing sides of the squeezable container. The proximal and distal edges and the first and second lateral edges of the container support frame define a central opening that provides access to an outer wall of the squeezable container. The outer wall of the squeezable container may be squeezed for dispensing the topical skin adhesive. The container support frame has an elongated handle that extends proximally from the proximal edge of the container support frame, which may be used for spreading the topical skin adhesive over a kin surface after it has been dispensed from the squeezable container.

Silicones, such as high viscosity silicones, may be used as a topical skin adhesive (TSA) for closing wounds. There are many challenges, however, associated with effectively mixing and spreading high viscosity silicones (e.g., silicones having >10,000 centipoise). For example, many existing systems are incapable of effectively mixing components to form high viscosity silicones, which results in poor, incomplete and/or long duration cure cycles. In addition, many existing mixing systems entrap air in the high viscosity silicone during mixing, which leads to the formation of bubbles in the high viscosity silicone. The presence of bubbles, and particularly relatively large bubbles, could compromise the uniformity, strength and adhesion of the TSA.

Another challenge confronted with existing systems is the ability to effectively apply and uniformly spread a high viscosity silicone before the high viscosity silicone fully cures. Thus, rapid mixing (i.e., on the order of seconds) followed by rapid application and spreading over tissue (e.g., a skin surface) is required to produce uniform and effective wound dressings.

Many high viscosity silicones are designed to cure at body temperature over a period of about three to five (3-5) minutes. In some instances, however, it may be desirable to use faster curing topical skin adhesives that cure in one minute or less.

Thus, in spite of the above-noted advances, there remains a need for improved systems, devices, and methods for effectively mixing two or more components that may be used as an adhesive for closing wounds. There also remains a need for improved systems, devices and methods for mixing wound closure adhesives that minimize the presence of air bubbles within the adhesives. In addition, there remains a need for improved systems, devices and methods for effectively applying and spreading wound closure adhesives over wounds. Furthermore, there remains a need for improved systems, devices and methods for shortening the curing time for wound closure adhesives after they have been applied onto tissue and skin surfaces for closing wounds.

SUMMARY OF THE INVENTION

Curable compositions, such as silicone-based topical skin adhesives, offer much promise and benefit including 1) significantly less tissue reaction, 2) increased flexibility, and 3) ease of application. Even greater benefits may be derived by accelerating the on-patient curing time from about three (3) minutes to one (1) minute or less. The present patent application discloses systems, devices and methods for attaining more efficient application of a curable composition and faster curing times for the applied curable composition.

In one embodiment, a system for dispensing a curable composition, such as a silicone-based topical skin adhesive, preferably includes a delivery device for expelling one or more components of the curable composition, a static mixer having a proximal end that is connected with a distal end of the delivery device for receiving the one or more components expelled from the delivery device, and a flexible spreader having a proximal end that is connected with a distal end of the static mixer. In one embodiment, the flexible spreader has a distal end including a flat dispensing opening, and a plurality of channels that extend through the flexible spreader to the flat dispensing opening.

In one embodiment, the delivery device contains at least one component of a curable composition. In one embodiment, the delivery device is configured to expel the at least one component of the curable composition from the delivery device and into the proximal end of the static mixer.

The curable composition may include one or more of the following components: polyurethane, acrylic, methyl methacrylate, silicone, condensation cured silicone, epoxy, polysulfide, and high viscosity curable biocompatible compositions having viscosities greater than 5000 cP.

In one embodiment, the curable composition may be used as a stand-alone component for sealing a wound, or used in conjunction with a surgical mesh that is a part of a reinforcing system.

In one embodiment, the curable composition preferably includes a cross-linkable silicone polymer having reactive functionalities, a silica-containing composition, a silicone cross-linking agent, and a catalyst. In one embodiment, the catalyst comprises a platinum tetramethyldivinyl disiloxane diethyl maleate complex having the formula:

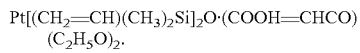

In one embodiment, the cross-linkable silicone polymer may be vinyl terminated polydialkylsiloxane, vinyl terminated polydimethylsiloxane, vinyl terminated polydiphenylsilane-dimethylsiloxane copolymer, vinyl terminated polyphenylmethylsiloxane, vinyl terminated polyfluoropropylmethyl-dimethylsiloxane copolymer, vinyl terminated polydiethylsiloxane, and/or SiH terminated polydimethyldisiloxane.

In one embodiment, the delivery device preferably includes a dual barrel syringe having a first syringe barrel containing a first component of the curable composition and a first plunger disposed within the first syringe barrel, and a second syringe barrel containing a second component of the curable composition and a second plunger disposed within the second syringe barrel. In one embodiment, the first and second plungers are moveable toward distal ends of the respective first and second syringe barrels for expelling the first and second components from the distal ends of the respective first and second syringe barrels and into the proximal end of the static mixer.

In one embodiment, the system desirably includes a tab that interconnects proximal ends of the first and second plungers for simultaneously moving the first and second plungers toward the distal ends of the respective first and second syringe barrels for simultaneously expelling the first and second components from the respective first and second barrels and into the static mixer.

In one embodiment, the static mixer desirably includes a static mixing tube having a proximal end with a proximal opening, a distal end with a distal opening, and a conduit that extends from the proximal opening to the distal opening. In one embodiment, at least one helical baffle is disposed within the conduit of the static mixing tube. The at least one helical baffle preferably includes helically wounds blades adapted to mix the first and second components together to form the curable composition as the first and second components flow through the static mixing tube.

In one embodiment, the system desirably includes the flexible spreader coupled with the distal end of the static mixer. In one embodiment, the flexible spreader desirably includes a flexible blade having a proximal end and a distal end. In one embodiment, the flexible blade desirably includes a first wall extending from the proximal end to the distal end of the flexible blade, and a second wall extending from the proximal end to the distal end of the flexible blade. In one embodiment, the plurality of channels desirably extend between the first and second walls to the flat dispensing opening at the distal end of the flexible spreader. The channels are used to direct the curable composition to the flat dispensing opening for dispensing the curable composition from the distal end of the flexible spreader. The plurality of channels preferably define tortuous flow paths extending between the first and second walls to the flat dispensing opening at the distal end of the flexible spreader. As the curable composition passes through the tortuous flow paths, any gas or air bubbles present in the curable composition are preferably removed and/or eliminated.

In one embodiment, the flexible blade may be made of silicone, rubber, and/or polymer materials. In one embodiment, the flexible blade is made of a material having a 0-80 durometer Shore A hardness rating.

In one embodiment, the flexible spreader desirably includes a plurality of spaced posts extending from the first wall to the second wall for defining the plurality of channels. In one embodiment, the first wall has an inner surface and the second wall has an inner surface that opposes the inner surface of the first wall. The spaced posts desirably extend from the inner surface of the first wall to the inner surface of the second wall. The spaced posts may have a matrix pattern and the channels extend between the spaced posts.

In one embodiment, the distance between the proximal ends of the first and second walls of the flexible blade is greater than the distance between the distal ends of the first and second walls of the flexible blade. Thus, the flexible blade may be thicker at the proximal end thereof and thinner at the distal end thereof.

In one embodiment, the flexible blade desirably has a first width at the proximal end thereof and a second width at the distal end thereof that is greater than the first width so that the distal end of the flexible blade is wider than the proximal end of the flexible blade.

In one embodiment, the flexible spreader enables medical personnel to uniformly apply the curable composition (e.g., topical skin adhesive) over a surface. In one embodiment, the distal end of the flexible spreader preferably includes a flat, elongated orifice that enables uniform application of a ribbon of a curable composition onto a pre-positioned reinforcing mesh, whereby the dispensed ribbon conforms to and matches the dimension of the reinforcing mesh. Moreover, once an initial ribbon of the curable composition has been applied to the mesh and/or adjacent tissue, a flexible blade of the flexible spreader may serve as a spatula or putty knife to further spread the curable composition to a uniform thickness while allowing blending within the mesh as well as onto the adjacent skin.

In one embodiment, the flexible spreader may be made of a soft (i.e., low durometer) elastic material. In one embodiment, the flat dispensing opening of the flexible spreader preferably has a length that is greater than a height or width of the dispensing opening (e.g., at least eight times longer than high/wide). In one embodiment, a major face of the flexible spreader may serve as a spreading surface. After application of the curable composition onto a surface, a spreading surface of the flexible spreader may be used to provide pressure to an uncured, curable composition to effectively compress and shear the curable composition to reduce porosity.

In one embodiment, the static mixer is a high throughput component and is preferably located between a distal end of a dispensing device (e.g., a double barrel syringe) and a proximal end of the flexible spreader. In one embodiment, during a dispensing operation, the static mixer preferably enables effective, uniform mixing of the curable composition within seconds, while minimizing the generation of air bubbles within the curable composition (e.g., a high viscosity silicone). The rapid and uniform mixing that occurs within the static mixer provides medical personnel with more time to apply the curable composition to tissue and more time to uniformly cure the curable composition.

In one embodiment, the static mixer and the flexible spreader operate together to optimize the ergonomics and usability of the systems and devices disclosed herein.

In one embodiment, the system desirably includes a hot gas blower configured to generate a hot gas stream that flows distally over the distal end of the flexible spreader. In one embodiment, the hot gas stream is preferably used to cure the curable composition after it has been dispensed from the flat dispensing opening of the flexible spreader.

In one embodiment, the hot gas blower may include a fan or blower that forces air across a heating element for heating the air, which is then directed onto a surface of the curable composition that has been applied to a skin surface or onto tissue. The hot gas blower may be a stand-alone device that has its own power source (e.g., a battery). In one embodiment, the hot gas blower may be an integral component of a system for dispensing a curable composition.

In one embodiment, the hot gas blower may be actuated during or after application of the curable composition, such as by engaging an actuator, a button or a lever. In one embodiment, the temperature of the hot gas stream may be regulated through the use of an integrated temperature measuring device, such as a thermistor, a thermocouple, and/or an infrared (IR) meter/pyrometer. In one embodiment, a signal generated by the temperature measuring device may be communicated to a circuit or an electronic component (e.g., a microprocessor), which may process the signal and, in turn, provide uniform and safe temperature control of the hot gas stream. In one embodiment, the temperature of the hot gas stream may be in the range of about 40-70 C., and more preferably in the range of about 45-60 C. In one embodiment, the temperature range of the hot gas stream is preferably selected and controlled to maximize the cure rate of the curable composition while avoiding tissue damage and/or patient discomfort.

In one embodiment, the hot gas blower may use a source gas (e.g., a compressed air cylinder that contains the source gas), which is preferably fed through the heating system for generating the hot gas stream that is directed onto the curable composition (e.g., a silicone-based TSA) applied to a surface (e.g., a skin surface; tissue) for promoting rapid curing. In one embodiment, the hot gas blower may be located adjacent the static mixer and proximal to the distal end of the flexible spreader.

The system disclosed herein may be used for treating a broad array of surgical and/or non-surgical anatomical regions. For example, the system may be used to apply a curable composition (e.g., a silicone based topical skin adhesive) to large incisions, or small incisions such as those formed during minimally invasive surgical procedures. In addition, diabetic and hard to heal ulcers may also benefit from the systems, devices and methods disclosed herein. In other embodiments, the systems may be used to dispense and apply a TSA to fix drains and other surgical accessories. The systems, devices and methods disclosed herein may also help medical personnel attain better cosmetic results than when using traditional TSAs.

In one embodiment, a system for dispensing a curable composition desirably includes a dual barrel syringe having a first syringe barrel containing a first component of a curable composition and a first plunger disposed within the first syringe barrel, and a second syringe barrel containing a second component of the curable composition and a second plunger disposed within the second syringe barrel.

In one embodiment, the system preferably includes a static mixer having a proximal end that is connected with distal ends of the respective first and second syringe barrels. The first and second plungers are preferably moveable toward the distal ends of the respective first and second syringe barrels for expelling the first and second components from the distal ends of the respective first and second syringe barrels and into the proximal end of the static mixer for mixing the first and second components to form the curable composition.

In one embodiment, the system desirably includes a flexible spreader having a proximal end that is connected with a distal end of the static mixer, a distal end including a flat dispensing opening, and a plurality of channels extending to the flat dispensing opening that are configured to deliver the curable composition from the static mixer to the flat dispensing opening.

In one embodiment, the system desirably includes a hot gas blower configured to generate a hot gas stream that flows distally beyond the distal end of the flexible spreader for curing the curable composition dispensed from the flat dispensing opening.

In one embodiment, the flexible spreader preferably includes a flexible blade having a proximal end and a distal end. In one embodiment, the flexible blade includes a first wall extending from the proximal end to the distal end of the flexible blade, a second wall extending from the proximal end to the distal end of the flexible blade, and a plurality of spaced posts extending from the first wall to the second wall for defining the plurality of channels extending between the first and second walls to the flat dispensing opening at the distal end of the flexible spreader.

In one embodiment, the spaced posts may be arrayed in a matrix pattern. In one embodiment, the plurality of channels may extend between the spaced post matrix to define tortuous flow paths for the curable composition as the composition flows through the flexible blade to the flat dispensing opening.

In one embodiment, the flexible spreader is made of a material having a 0-80 durometer Shore A hardness rating, such as silicone, rubber, and/or polymer materials.

In one embodiment, the distance between the proximal ends of the first and second walls of the flexible blade is greater than the distance between the distal ends of the first and second walls of the flexible blade. Thus, the proximal end of the flexible blade may be thicker than the distal end of the flexible blade.

In one embodiment, the flexible blade has a first width at the proximal end thereof and a second width at the distal end thereof that is greater than the first width so that the distal end of the flexible blade is wider than the proximal end of the flexible blade.

In one embodiment, a method of dispensing a curable composition may including expelling two components from a delivery device into a static mixer, mixing the two components together within the static mixer to form a curable composition (e.g., a silicone-based topical skin adhesive), directing the curable composition into a flexible spreader having a plurality of channels that extend to a flat dispensing opening located at a distal end of the flexible spreader, and dispensing the curable composition from the flat dispensing opening onto a surface, such as a skin surface.

In one embodiment, the method may include using one or more outer surfaces of the flexible spreader for spreading the dispensed curable composition onto the surface.

In one embodiment, the method may include directing a stream of hot gas or air onto the curable composition for curing the curable composition.

DETAILED DESCRIPTION OF PREFERRED EMBODIMENTS

Figure 1:
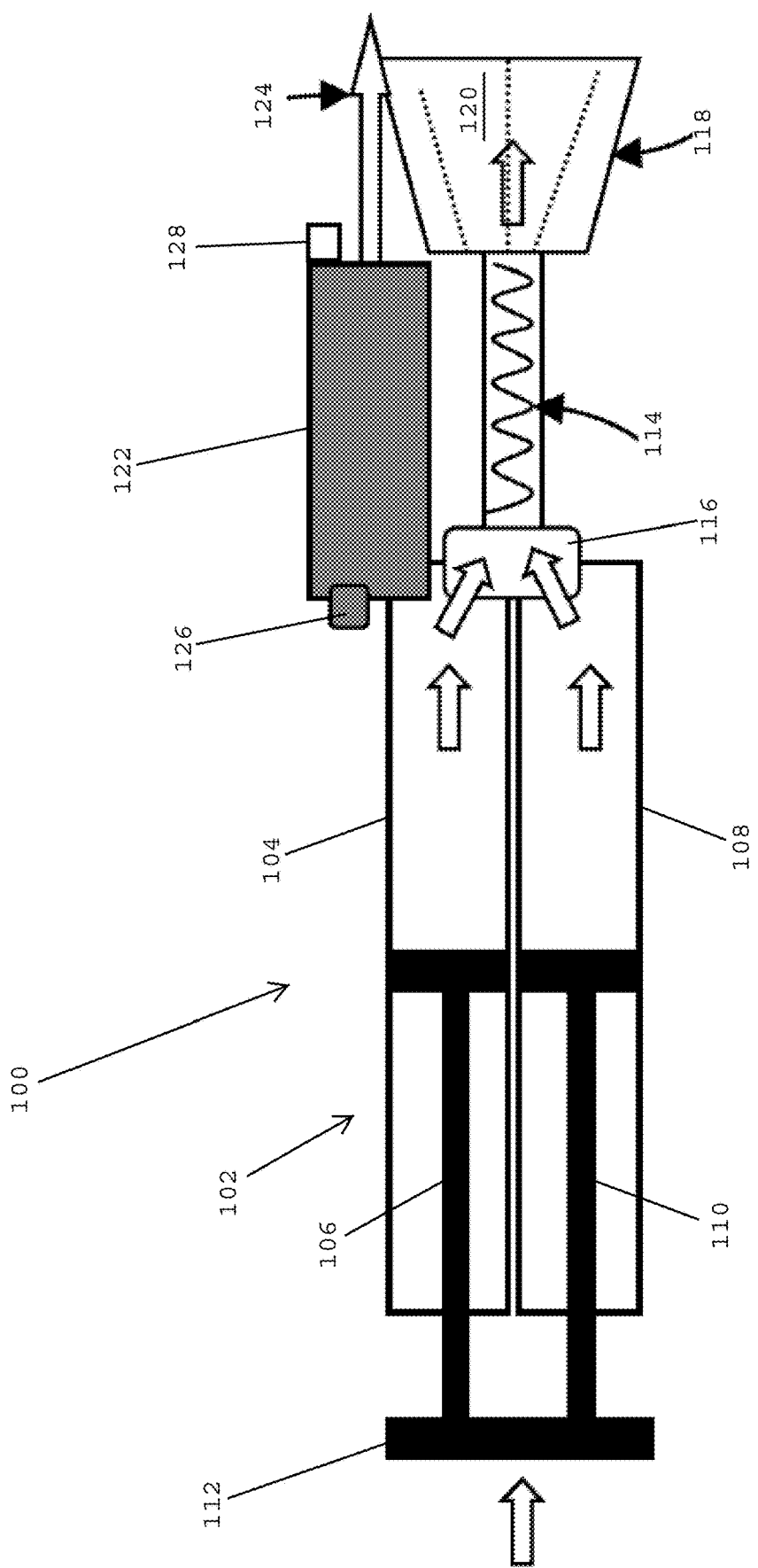
FIG. 1 is a schematic view of a system for dispensing and curing a high viscosity curable composition, the system including a double barrel syringe, a hot gas blower, a static mixer, and a flexible spreader, in accordance with one embodiment of the present patent application.

Referring to FIG. 1, in one embodiment, a system 100 for dispensing a curable composition, such as a high-viscosity curable composition, and more preferably a silicone-based high-viscosity curable composition, preferably includes a double barrel syringe 102 having a first barrel 104 with a first plunger 106 for dispensing a first component of the curable composition, and a second barrel 108 with a second plunger 110 for dispensing a second component of the curable composition. The first and second components are adapted to be mixed together for forming the curable composition, which may be used as a topical skin adhesive (TSA) and/or a wound adhesive. In one embodiment, the first and second plungers 106, 110 are preferably joined together via a syringe actuator 112 (e.g., a depressible thumb tab) that may be pressed in a distal direction DIR1 for simultaneously expelling the first component from the distal end of the first barrel 104 and the second component from the distal end of the second barrel 108.

In one embodiment, the system 100 for dispensing the curable composition may include a static mixer 114 that is located downstream from the distal ends of the respective first and second barrels 104, 108. In one embodiment, a connector 116 preferably couples the distal ends of the respective first and second barrels 104, 108 with the proximal end of the static mixer 114. In one embodiment, the first and second components that are expelled from the distal ends of the first and second barrels 104, 108 are desirably mixed together within the static mixer 114 for forming the curable composition.

In one embodiment, the system 100 for dispensing the curable composition preferably includes a flexible spreader 118, such as a component having the shape of a spatula, a spackle spreader and/or a putty knife, which is desirably connected to a distal end of the static mixer for dispensing the curable composition that is mixed within the static mixer 114. In one embodiment, the flexible spreader 118 may have a flexible blade 120 with an elongated, flat dispensing opening located at a distal end thereof for dispensing the curable composition onto a surface (e.g., a skin surface, tissue, a wound). The one embodiment, the curable composition may be dispensed as a ribbon of curable composition having a length and a width. In one embodiment, the mixture of the first and second components that is expelled from a distal end of the static mixture is forced through the flexible blade 120 of the flexible spreader 118 for being dispensed from an elongated, flat dispensing opening located at the distal end of the flexible blade. The flexible blade 120 may be used for spreading the dispensed curable composition over a surface, such as a skin surface or a surgical mesh applied over tissue. In one embodiment, the flexible spreader and/or the flexible blade may be made of silicone, rubber, or a polymer material.

In one embodiment, the system 100 for dispensing a curable composition preferably includes a hot gas blower 122 that desirably generates a stream of hot gas 124 (e.g., ambient air; an inert gas) that is directed in the distal direction DIR1 for curing the curable composition that is dispensed from the distal end of the flexible blade 120 of the flexible spreader 118. In one embodiment, the hot gas blower 122 preferably includes an actuator 126 (e.g., a button) that may be in engaged to actuate the hot gas blower for generating a hot gas stream 124 that is dispensed in the distal direction DIR1 toward the distal end of the flexible blade 120 of the flexible spreader 118. In one embodiment, the hot gas blower 122 may be powered by an electrical power cord or a power source (e.g., a battery).

In one embodiment, the system 100 for dispensing a curable composition preferably includes a temperature sensor 128 that desirably monitors the temperature level of the hot gas 124 that is dispensed from the hot gas blower 122. The temperature sensor 128 may be located on the hot gas blower 122. Monitoring and controlling the temperature level of the hot gas that is discharged by the hot gas blower preferably insures that the temperature level of the hot gas 124 is maintained within a safe range for not damaging the patient's tissue and/or is maintained within a preferred temperature range for efficiently and effectively curing the curable composition.

Figure 2A:
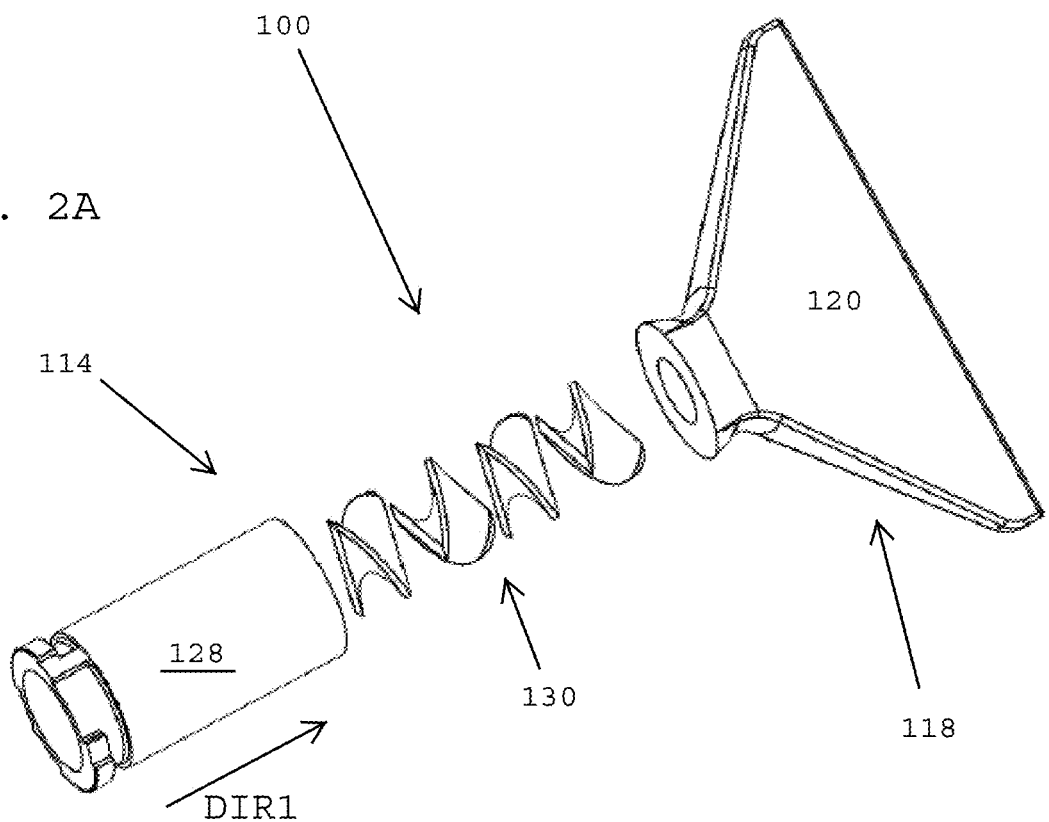
FIG. 2A is an exploded view of components of a system for dispensing and curing a high viscosity curable composition including a static mixing tube, a helical baffle, and a flexible spreader, in accordance with one embodiment of the present patent application.
Figure 2B:
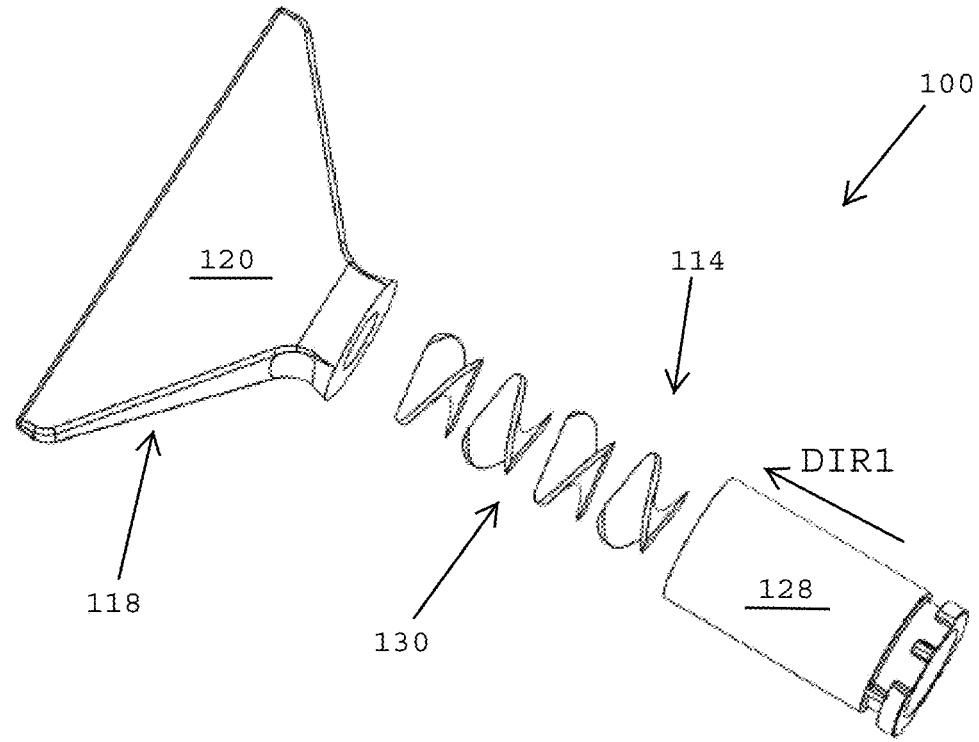
FIG. 2B is another exploded view of the static mixing tube, the helical baffle, and the flexible spreader shown in FIG. 2A.

Referring to FIGS. 2A and 2B, in one embodiment, the system 100 for dispensing a curable composition preferably includes the static mixer 114 and the flexible spreader 118 coupled with the distal end of the static mixer 114. In one embodiment, the static mixer 114 desirably includes a static mixing tube 128 and a helical baffle 130 disposed inside the static mixing tube 128 for mixing together the two components that are expelled from the first and second syringe barrels 104, 108 (FIG. 1) to generate a high viscosity curable composition (e.g., a silicone-based, high viscosity curable composition) that is dispensed via the flexible blade 120 of the flexible spreader 118. In one embodiment, the helical baffle 130 of the static mixer 114 may include two or more helical baffle components that are disposed inside a conduit of the static mixing tube 128. In one embodiment, the helical baffle 130 may be a unitary structure comprising a single, elongated helical baffle. In one embodiment, the two components of the high viscosity curable composition are preferably directed into the proximal end of the static mixing tube 128 in the distal direction DIR1 for being mixed together by the blades of the helical baffle 130, and then directed into the proximal end of the flexible spreader for being dispensed from the elongated, flat dispensing opening located at the distal end of the flexible blade 120 of the flexible spreader 118.

Figure 3A:
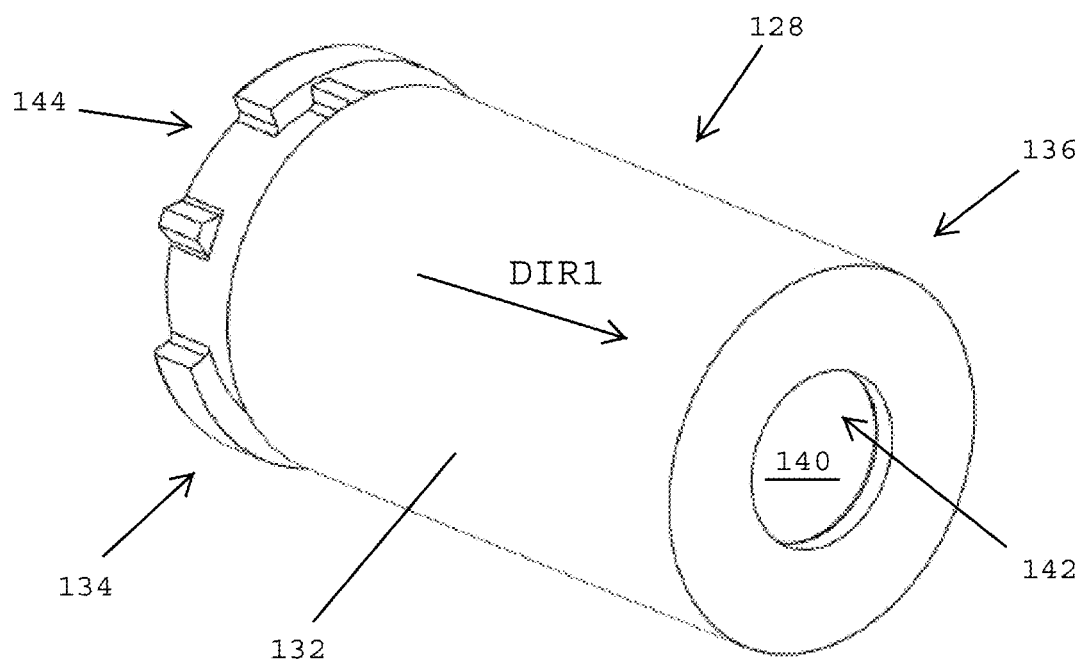
FIG. 3A is a perspective view of a distal end of the static mixing tube shown in FIGS. 2A and 2B.
Figure 3B:
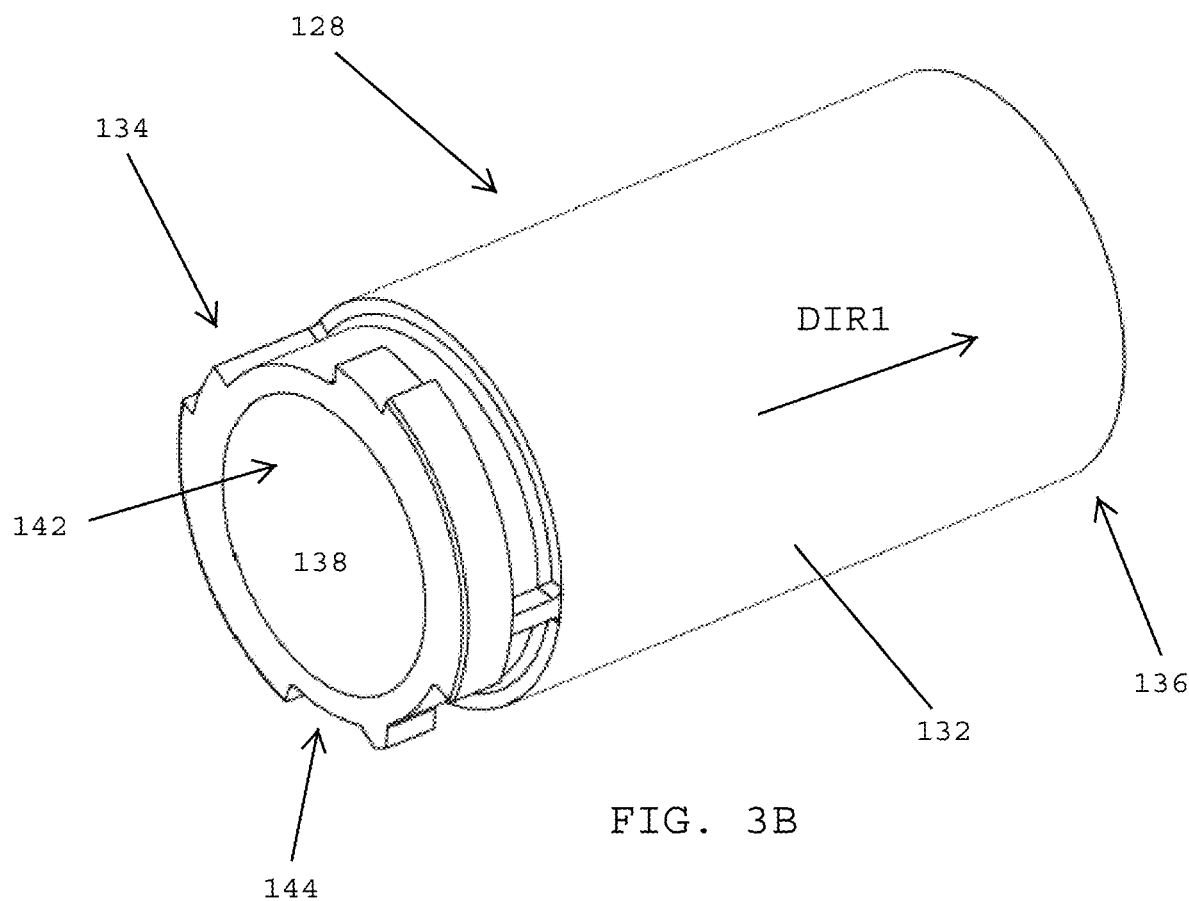
FIG. 3B is a perspective view of a proximal end of the static mixing tube shown in FIGS. 2A and 2B and 3A.

Referring to FIGS. 3A and 3B, in one embodiment, the static mixing tube 128 desirably includes a tubular-shaped outer wall 132 that extends from a proximal end 134 to a distal end 136 of the static mixing tube. In one embodiment, the static mixing tube 128 preferably has a proximal opening 138 located at the proximal end 134 thereof, which is in communication with the distal ends of the first and second syringe barrels 104, 108 (FIG. 1), and a distal opening 140 located at the distal end 136 thereof. The static mixing tube 128 preferably includes an elongated conduit 142 that extends from the proximal end 134 to the distal end 136 thereof. The helical baffle 130 (FIGS. 2A and 2B) is preferable disposed within the elongated conduit 142 for mixing the two components together as they flow in the distal direction DIR1 through the static mixing tube 128.

In one embodiment, the proximal end 134 of the static mixing tube 128 preferably includes a connecting structure 144 formed on the outer surface of the tubular-shaped wall 132 for connecting the proximal end 134 of the static mixing tube 128 with the connector 116 located at the distal ends of the respective first and second syringe barrels 104, 108 (FIG. 1).

Figures 3C, 3D:
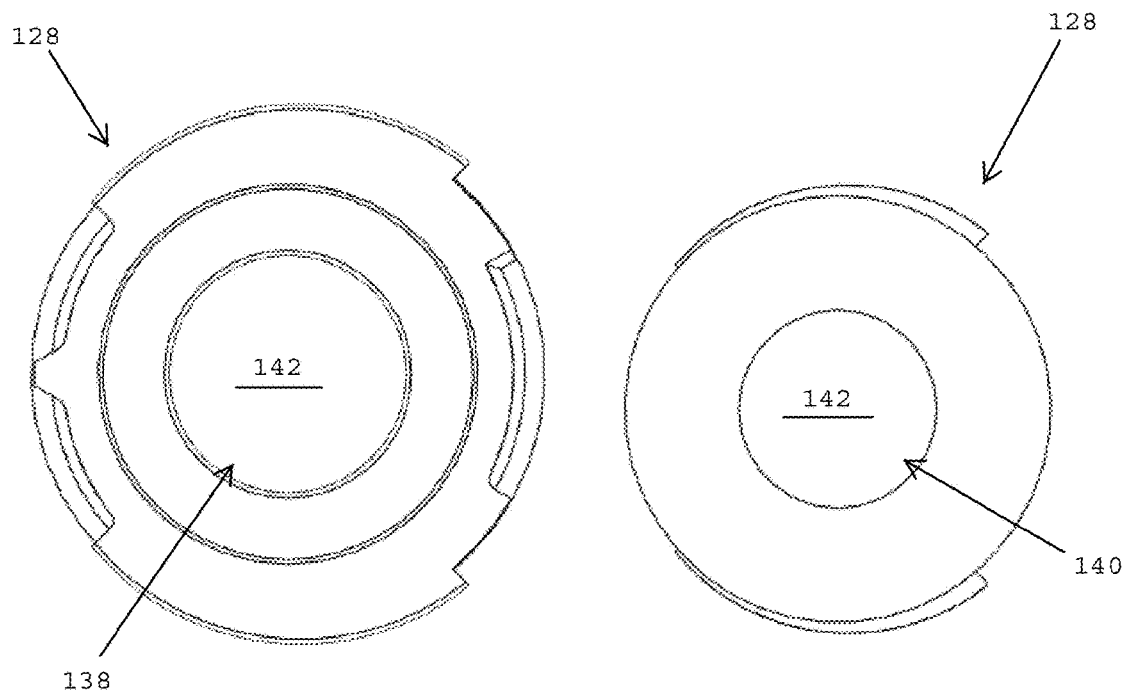
FIG. 3C is a proximal end view of the static mixing tube shown in FIGS. 3A and 3B.
FIG. 3D is a distal end view of the static mixing tube shown in FIGS. 3A-3C.
Figure 3E:
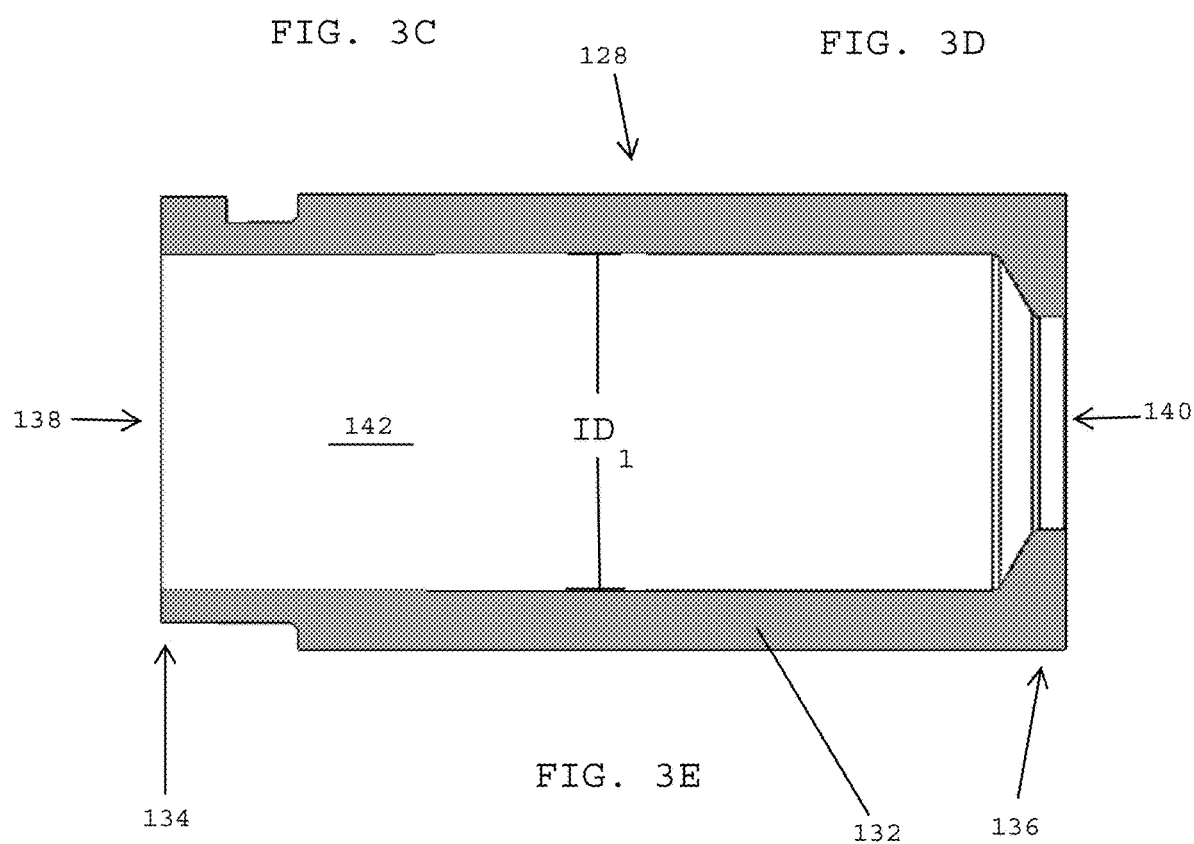
FIG. 3E is a cross-sectional view of the static mixing tube shown in FIGS. 3A-3D.

Referring to FIGS. 3C-3E, in one embodiment, the elongated conduit 142 of the static mixing tube 128 desirably extends along the length of the static mixing tube 128. In one embodiment, the elongated conduit 142 preferably extends from the proximal opening 138 at the proximal end 134 of the static mixing tube 128 to the distal opening 140 at the distal end 136 of the static mixing tube 128.

Referring to FIG. 3E, in one embodiment, the inner surface of the tubular shaped outer wall 132 preferably defines an inner diameter $ID_1$ that is dimensioned to receive the helical baffle 130 (FIGS. 2A-2B).

Figure 4A:
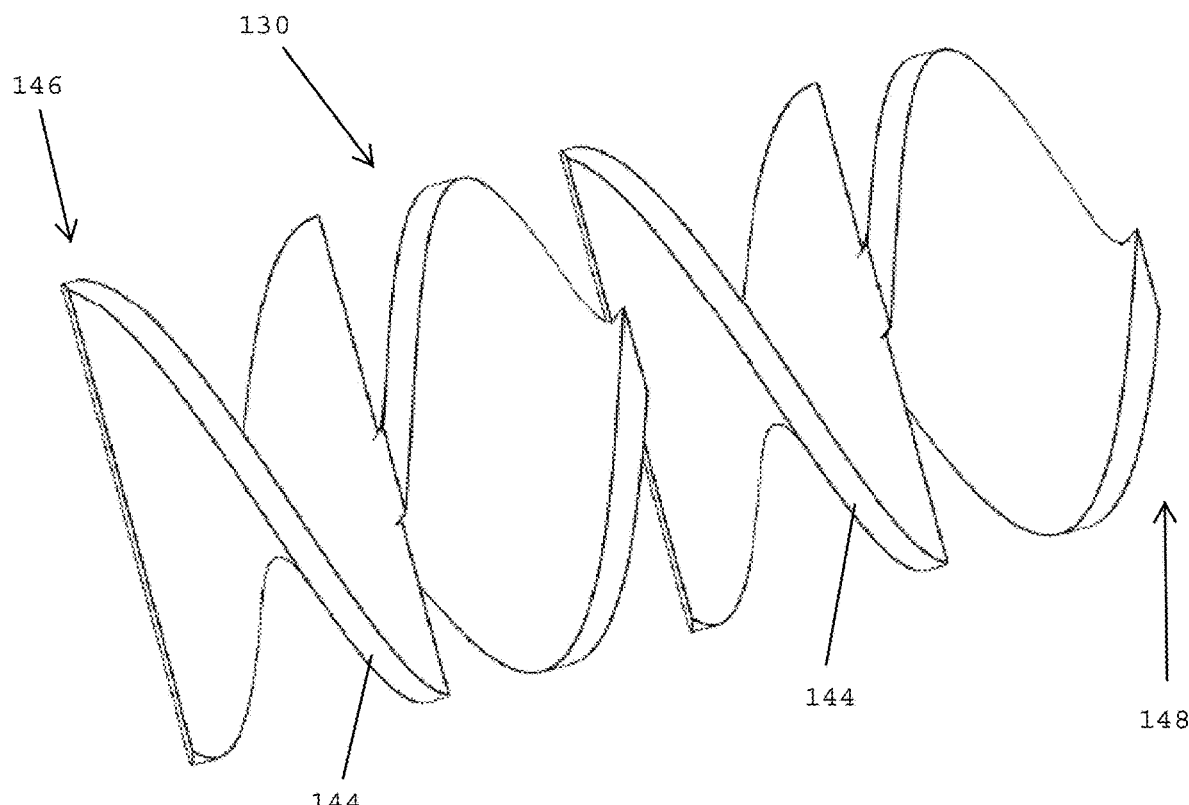
FIG. 4A is a perspective view of the helical baffle shown in FIGS. 2A and 2B.
Figure 4B:
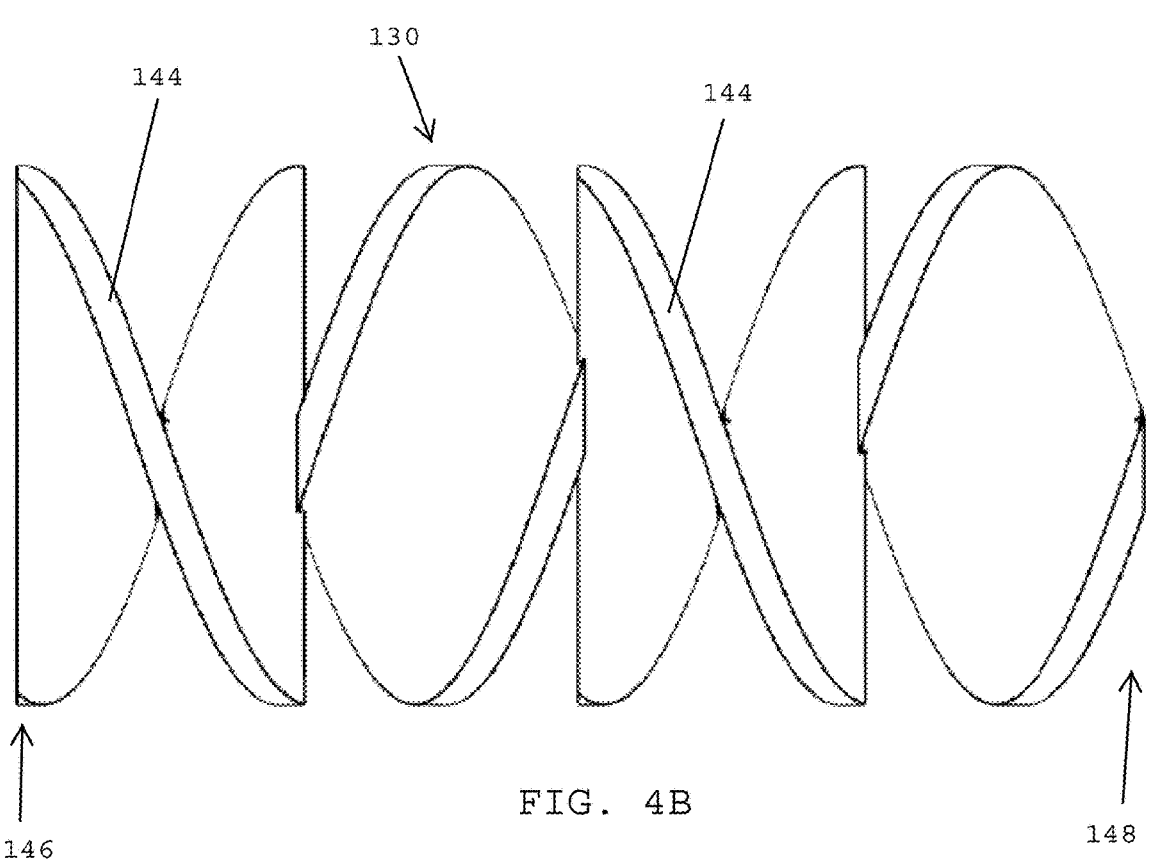
FIG. 4B is a side elevation view of the helical baffle shown in FIG. 4A.

Referring to FIGS. 4A-4B, in one embodiment, the helical baffle 130 preferably includes a plurality of helically wound blades 144 that extend from a proximal end 146 to a distal end 148 of the helical baffle. In one embodiment, the helically wound blades 144 of the helical baffle 130 preferably have a height defining an outer diameter $OD_1$ that substantially matches the inner diameter $ID_1$ of the elongated conduit 142 of the static mixing tube 128 (FIG. 3E).

Figure 5:
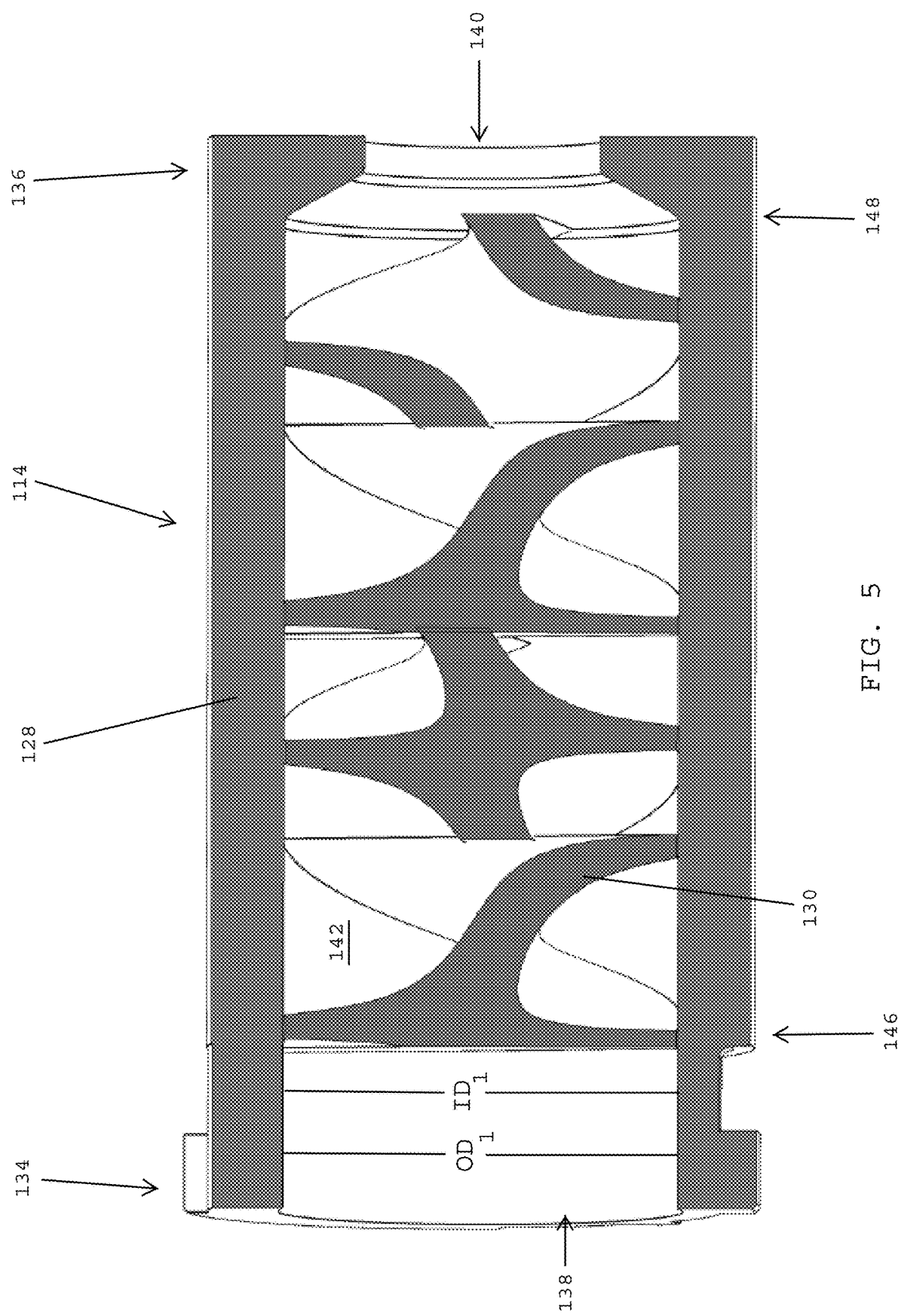
FIG. 5 is a cross-sectional view of the static mixing tube of FIGS. 3A-3E after the helical baffle of FIGS. 4A-4B has been disposed inside the static mixing tube, in accordance with one embodiment of the present patent application.

Referring to FIG. 5, in one embodiment, the helical baffle 130 is preferably assembled with the static mixing tube 128 by inserting the helical baffle 130 into the elongated conduit 142, which is surrounded by the barrel-shaped wall 132 of the static mixing tube 128. In one embodiment, the proximal end 146 of the helical baffle 130 is preferably located adjacent the proximal opening 138 of the static mixing tube 128 and the distal end 148 of the helical baffle 130 is preferably located adjacent the distal opening 140 of the static mixing tube 128. In one embodiment, the helical baffle 130 has an outer diameter $OD_1$ that substantially matches the inner diameter $ID_1$ of the elongated conduit 142 of the static mixing tube 128.

Figure 6A:
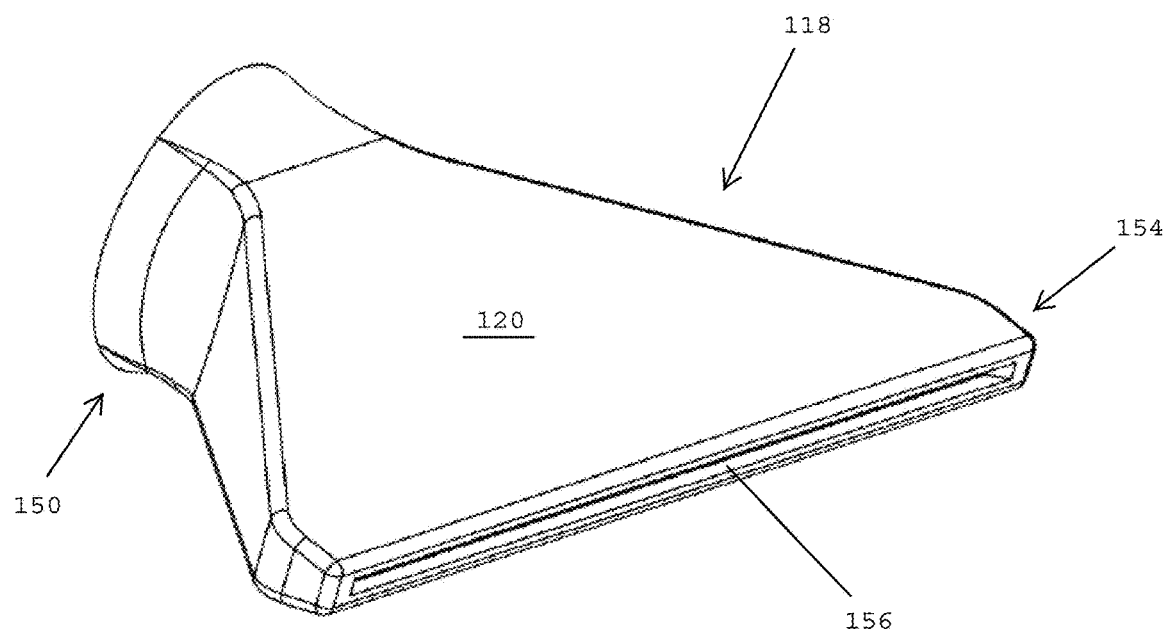
FIG. 6A is a perspective view of a distal end of the flexible spreader shown in FIG. 1, in accordance with one embodiment of the present patent application.
Figure 6B:
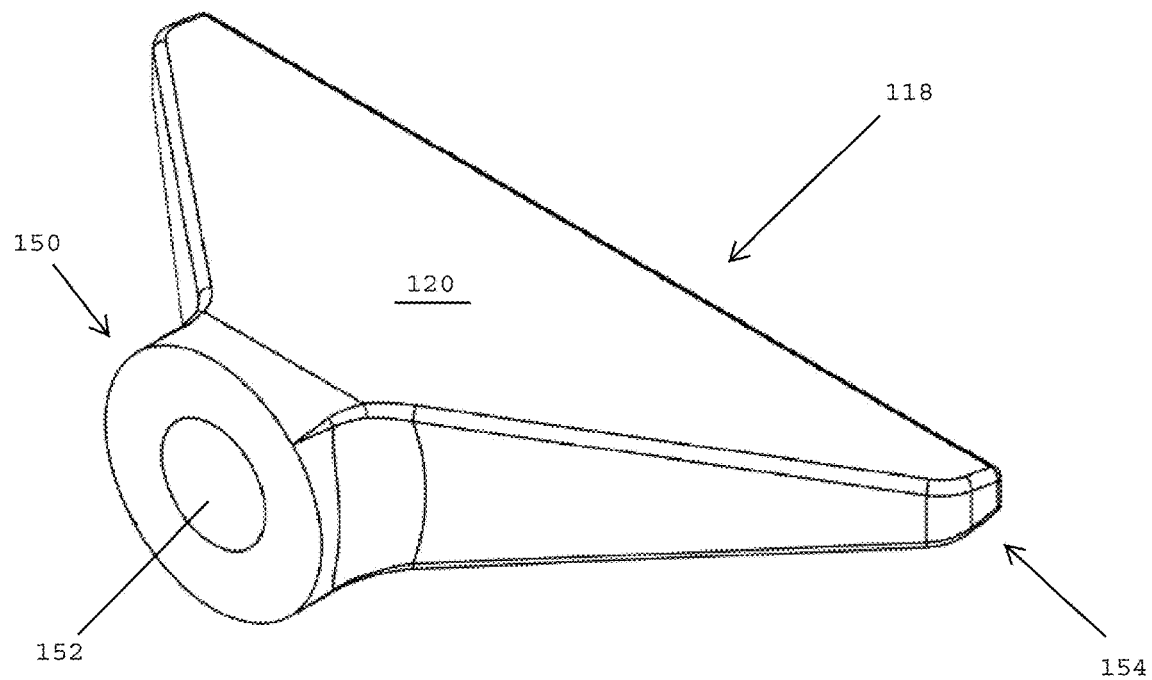
FIG. 6B is a perspective view of a proximal end of the flexible spreader shown in FIG. 6A.

Referring to FIGS. 6A and 6B, in one embodiment, the flexible spreader 118 preferably includes the flexible blade 120 that is adapted to spread a curable composition that is dispensed from a distal end of the flexible spreader. In one embodiment, the flexible spreader 118 preferably has a proximal end 150 including a proximal opening 152 and the distal end 154. The distal end of the flexible blade 120 preferably includes an elongated, flat dispensing opening 156 that extends across the width of the flexible blade 120 at the distal end of the flexible blade. In one embodiment, after the first and second components of a high viscosity curable composition have been mixed together within the static mixing tube shown and described above in FIGS. 3A-3E, 4A-4B, and 5, the curable composition is directed into the proximal opening 152 at the proximal end 150 of the flexible spreader 118 for being dispensed from the elongated, flat dispensing opening 156 located at the distal end of the flexible blade 120. In one embodiment, the elongated, flat dispensing opening facilitates dispensing a curable composition (e.g., a ribbon of a curable composition having a length and a width) onto a surface (e.g., a skin surface), whereupon the flexible spreader may be used to spread the curable composition over the surface.

Figure 6C:
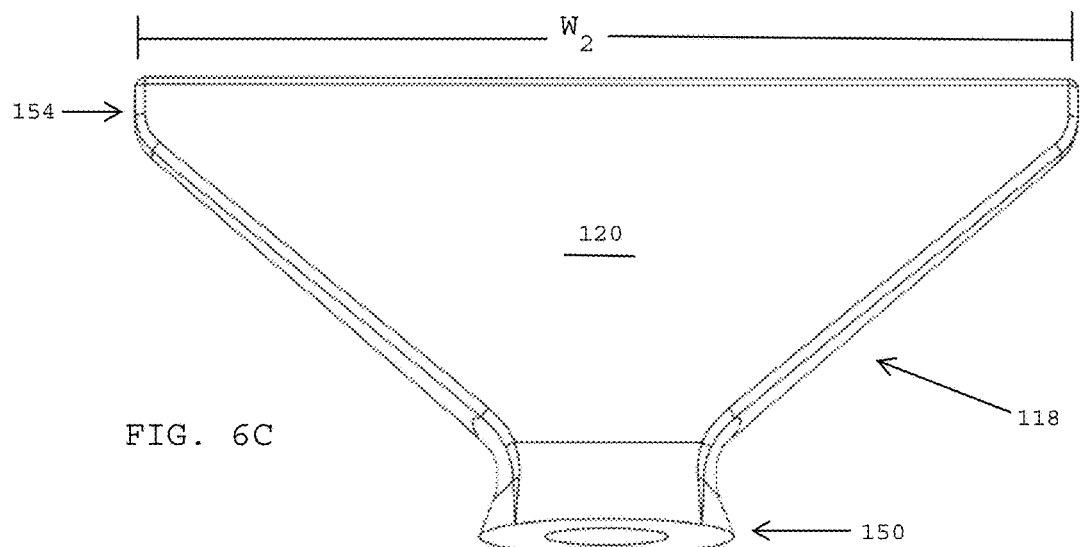
FIG. 6C is a top plan view of the flexible spreader shown in FIGS. 6A and 6B.

Referring to FIG. 6C, in one embodiment, the flexible spreader 118 preferably includes the flexible blade 120 that tapers outwardly (i.e., in a lateral direction) between the proximal end 150 and the distal end 154 of the flexible spreader 118. In one embodiment, the flexible blade 120 has a first width $W_1$ located at the proximal end of the flexible blade 120 and a second width $W_2$ located at the distal end of the flexible blade 120 that is greater than the first width $W_1$. In one embodiment, the second width $W_2$ at the distal end of the flexible blade 120 is preferably about 1.0-7.5 cm or greater, and more preferably about 2.5-4.0 cm. In one embodiment, the flexible blade 120 may have a shape that is similar to that of a spatula, a spackle spreader and/or a putty knife, which may be used for spreading a curable composition.

Figure 6D:
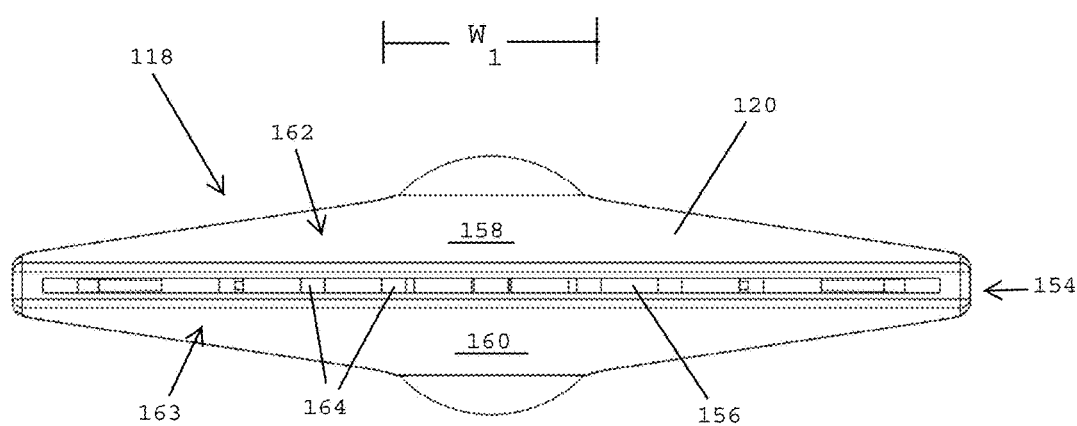
FIG. 6D is a distal end view of the flexible spreader shown in FIGS. 6A-6C.

Referring to FIG. 6D, in one embodiment, the distal end 154 of the flexible blade 120 preferably includes the elongated, flat dispensing opening 156 that is adapted to dispense the curable composition from the distal end 154 of the flexible spreader 118. In one embodiment, the flexible blade 120 of the flexible spreader 118 preferably includes a first wall 158 that defines a first end (e.g., an upper end) of a flow channel for the curable composition that passes through the flexible blade and a second wall 160 that defines a second end (e.g., a lower end) of the flow channel for the curable composition that passes through the flexible blade. The first and second walls 158, 160 are preferably spaced from one another to define the flow path for the curable composition that flows distally through the flexible blade 120. In one embodiment, as the curable composition flows from the proximal end to the distal end of the flexible blade 120, the curable composition flows between the first wall 158 and the second wall 160 for being directed toward the elongated, flat dispensing opening 156 that is located at the distal end 154 of the flexible blade 120.

In one embodiment, the first wall 158 of the flexible blade 120 preferably has a first major surface 162 and the second wall 160 of the flexible blade 120 preferably has a second major surface 163, whereby the first and second major surfaces 162, 163 are outer surfaces of the flexible blade that may be used for spreading the curable composition after it has been dispensed from the elongated, flat dispensing opening 156.

In one embodiment, the flexible spreader 118 preferably includes a plurality of spaced posts 164 that extend from an inner surface of the first wall 158 to an opposing, inner surface of the second wall 160. The posts 164 preferably span the space that is present between the first wall 158 and the second wall 160 to form a plurality of flow channels for the curable composition that have tortuous pathways between the proximal and distal ends of the flexible spreader 118. The flow channels preferably define the tortuous pathways for the flowing curable composition, which are adapted to breakup and/or eliminate any air or gas bubbles that are present in the curable composition before it is dispensed from the elongated, flat dispensing opening 156 of the flexible spreader 118.

Figure 6E:
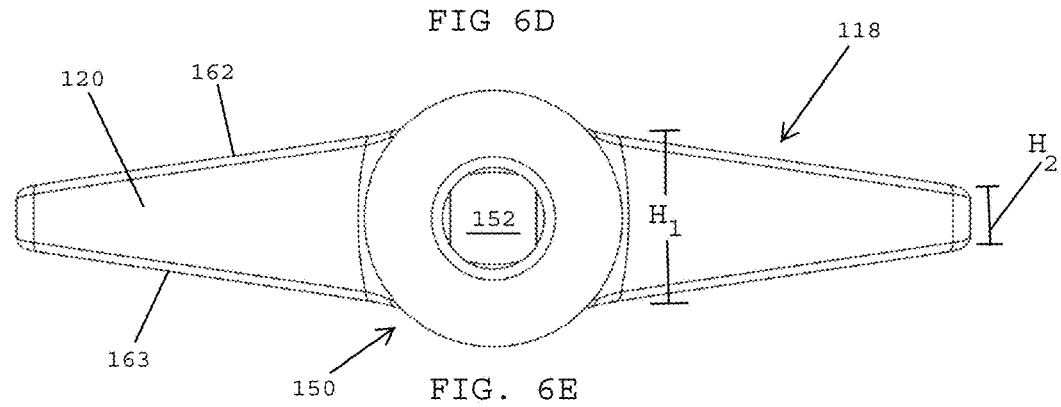
FIG. 6E is a proximal end view of the spreader shown in FIGS. 6A-6D.

Referring to FIG. 6E, in one embodiment, the proximal end 150 of the flexible spreader 118 preferably includes the proximal opening 152 that is adapted to receive the curable composition that is dispensed from the distal end of the static mixer 114 (FIG. 1). In one embodiment, the flexible blade 120 may be thicker at a central region thereof and thinner at outer regions (i.e., lateral regions) thereof. In one embodiment, the central region of the flexible blade 120 has a first height $H_1$ that is greater than the second height $H_2$ of the lateral regions of the flexible blade 120.

Figure 6F:
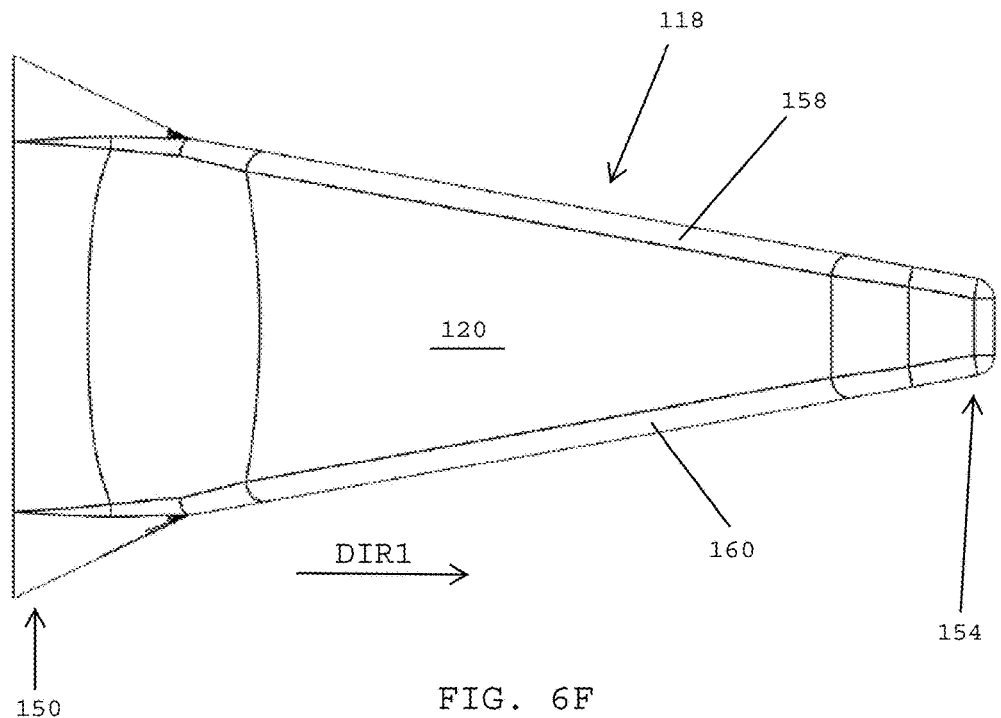
FIG. 6F is a side elevation view of the flexible spreader shown in FIGS. 6A-6E.
Figure 6G:
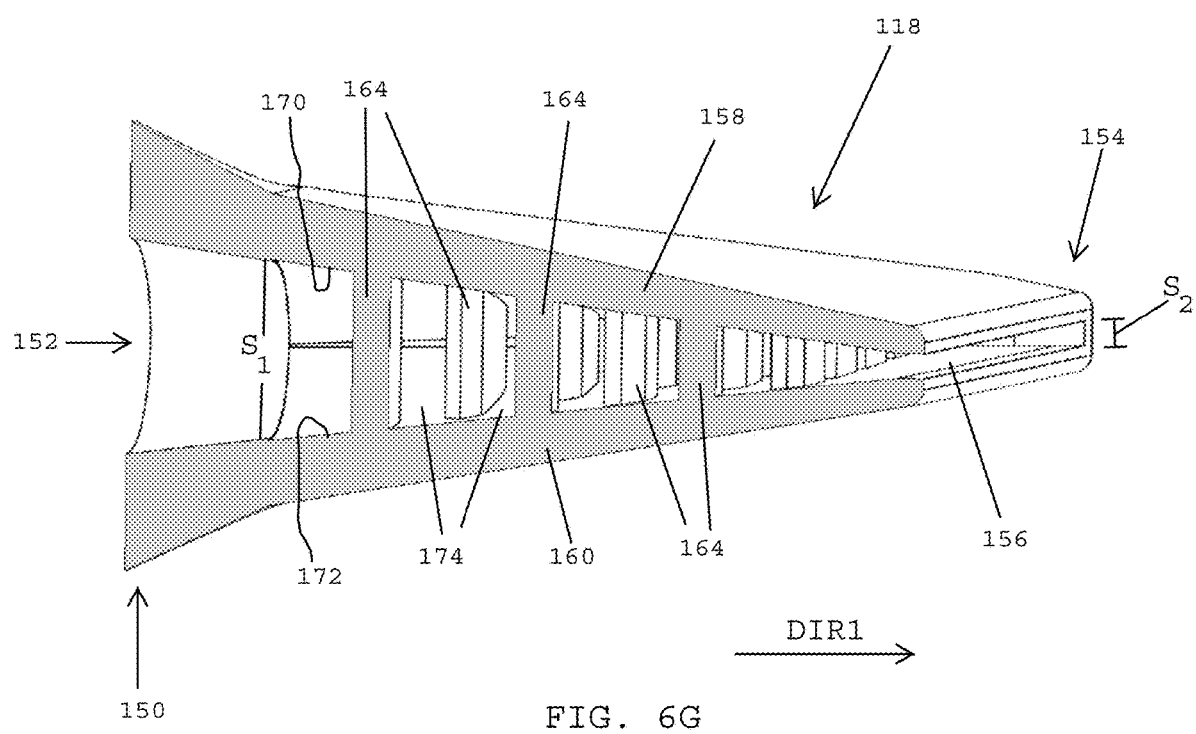
FIG. 6G is a cross-sectional view of the flexible spreader shown in FIGS. 6A-6F.

Referring to FIGS. 6F and 6G, in one embodiment, the flexible spreader 118 preferably includes the proximal end 150 having the proximal opening 152 and the distal end 154 having the elongated, flat dispensing opening 156. The flexible spreader 118 desirably includes the flexible blade 120 having the first wall 158 that is spaced away from the second wall 160 so that the curable composition that is introduced into the proximal opening 152 may flow between an inner surface 170 of the first wall 158 and an opposing inner surface 172 of the second wall 160 for being dispensed from the elongated, flat dispensing opening 156 that is located at the distal end 154 of the flexible spreader 118.

In one embodiment, the first and second walls 158, 160 of the flexible blade 120 preferably taper inwardly toward one another from the proximal end 150 of the flexible spreader 118 to the distal end 154 of the flexible spreader 118. As a result, the spacing $S_1$ between proximal ends of the first and second walls 158, 160 is greater than the spacing $S_2$ between distal ends of the first and second walls 158, 160. In one embodiment, the gap or spacing $S_2$ of the flat dispensing opening is desirably about 0.5-3.0 mm.

In one embodiment, the flexible spreader 118 preferably includes a plurality of spaced posts 164 that extend from the first wall 158 to the second wall 160 of the flexible blade 120 to form the plurality of narrow channels 174 that extend between the posts 164 for breaking up any air or gas bubbles that are present in the curable composition as the curable composition flows distally in the direction DIR1 from the proximal end 150 to the distal end 154 of the flexible spreader 118.

Figure 7A:
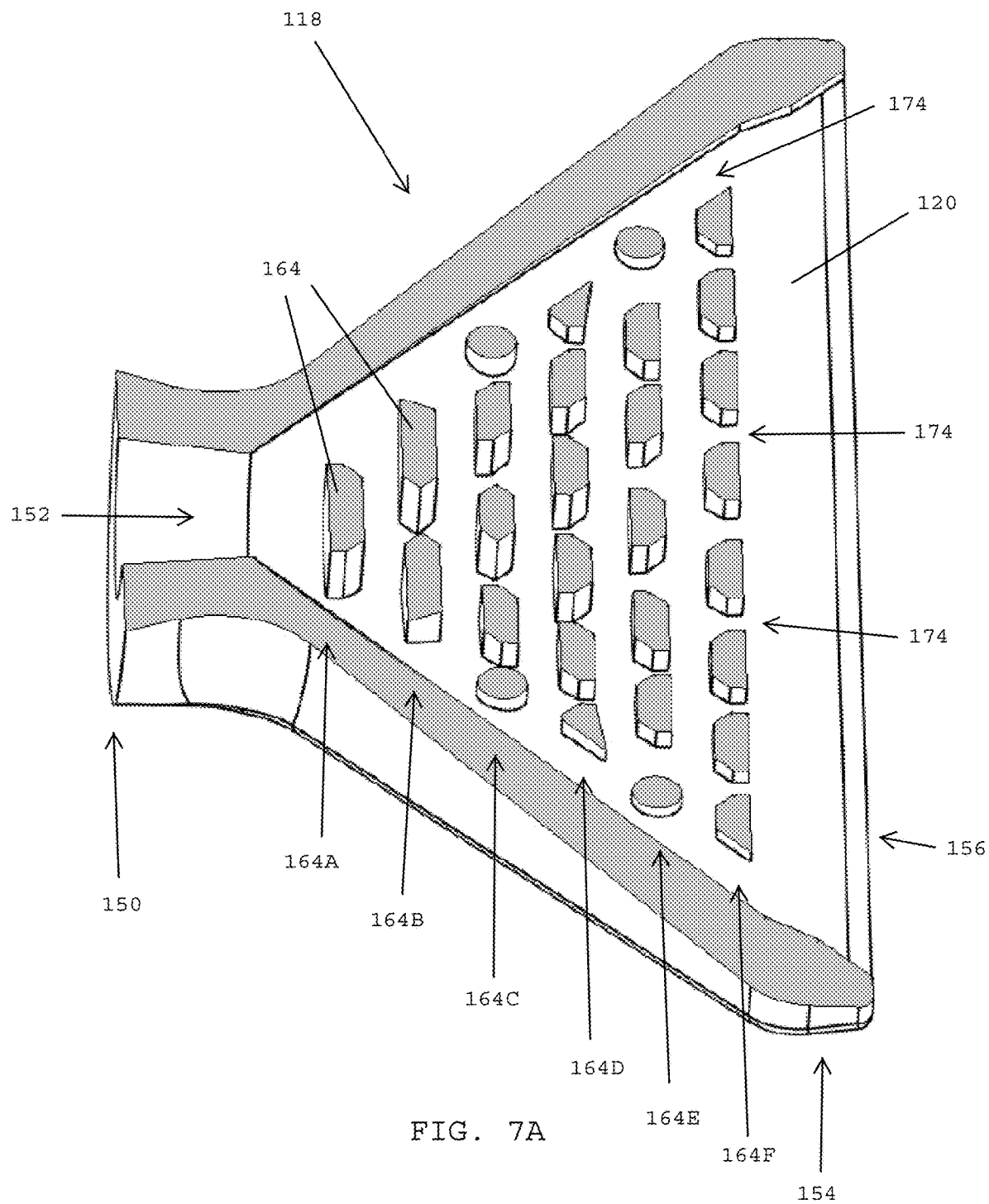
FIG. 7A is a cross-sectional view of the flexible spreader shown in FIGS. 6A-6G, in accordance with one embodiment of the present patent application.
Figure 7B:
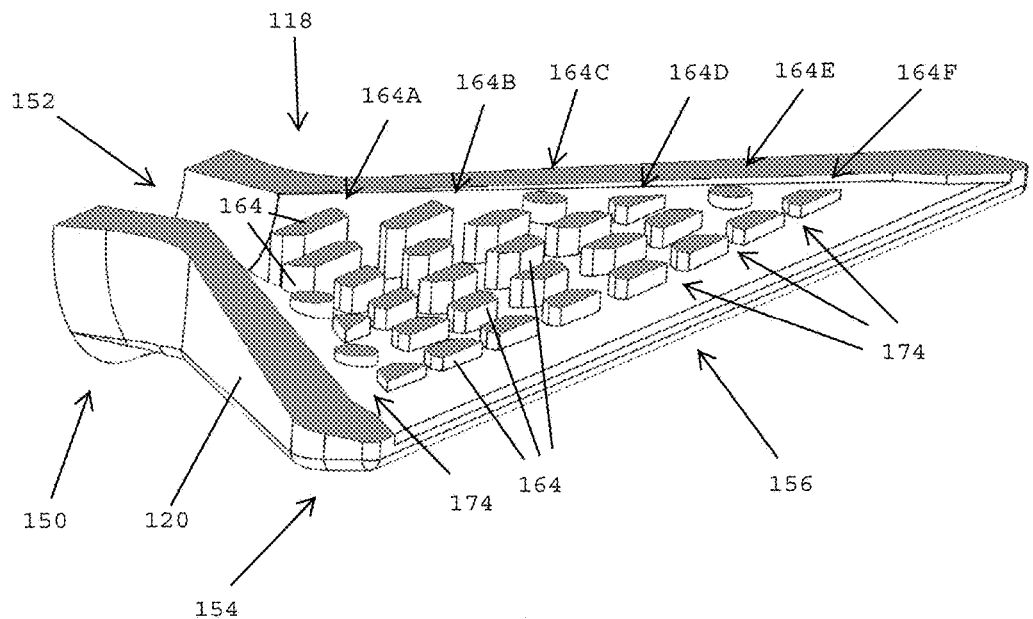
FIG. 7B is another view of the flexible spreader shown in FIG. 7A.
Figure 7C:
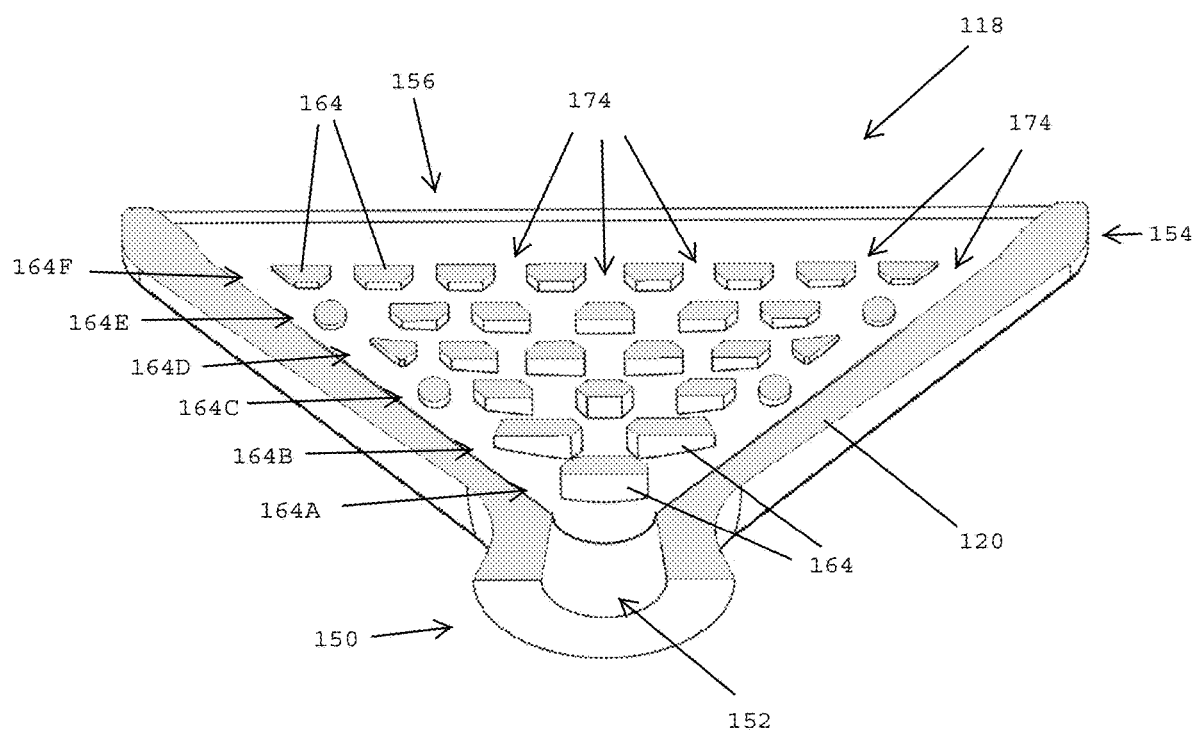
FIG. 7C is yet another view of the flexible spreader shown in FIGS. 7A and 7B.

Referring to FIGS. 7A-7C, in one embodiment, the flexible spreader 118 preferably includes the plurality of posts 164 that are spaced from one another between the proximal end 150 and the distal end 154 of the flexible blade 120. In one embodiment, the plurality of posts 164 are spaced from one another for defining the plurality of narrow flow channels 174 that are located between the spaced posts 164. The narrow flow channels 174 define separate and distinct tortuous pathways for the curable composition as it flows in the distal direction DIR1 for being dispensed through the elongated, flat dispensing opening 156 located at the distal end of the flexible blade 120 of the flexible spreader 118.

In one embodiment, the spaced posts 164 may be divided into rows of posts 164A-164F, whereby the posts in any one row have heights that are greater (i.e., taller) in the center of the flexible blade 120 and smaller (i.e., shorter) in the lateral regions of the flexible blade 120. In one embodiment, the posts 164 within any one row may become progressively shorter when moving from a central region of the row to outer, lateral regions of the row.

Figure 8A:
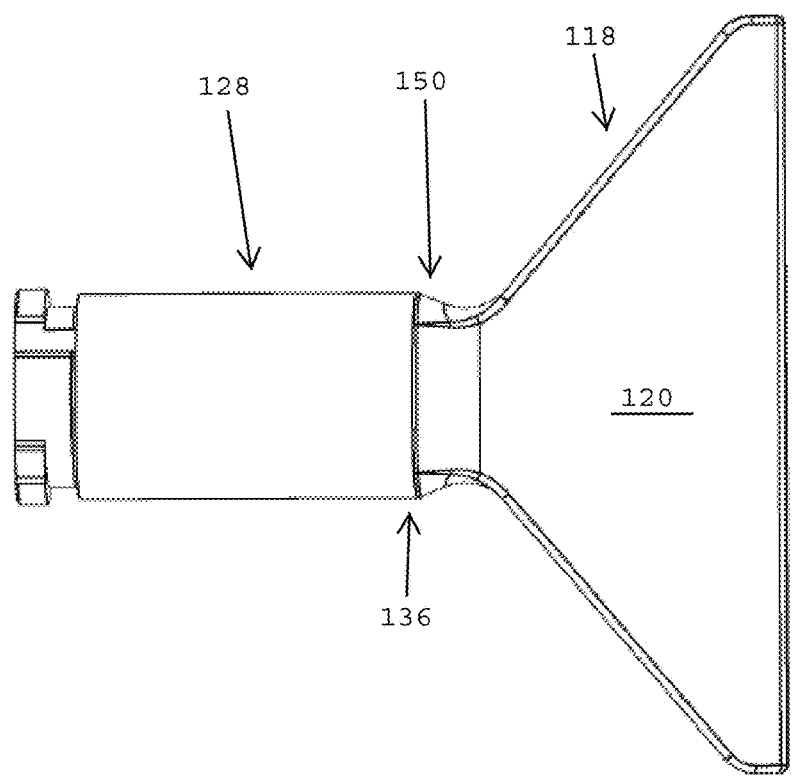
FIG. 8A is a top plan view of the flexible spreader of FIGS. 6A-6G assembled with a distal end of the static mixing tube of FIGS. 3A-3E, in accordance with one embodiment of the present patent application.
Figure 8B:
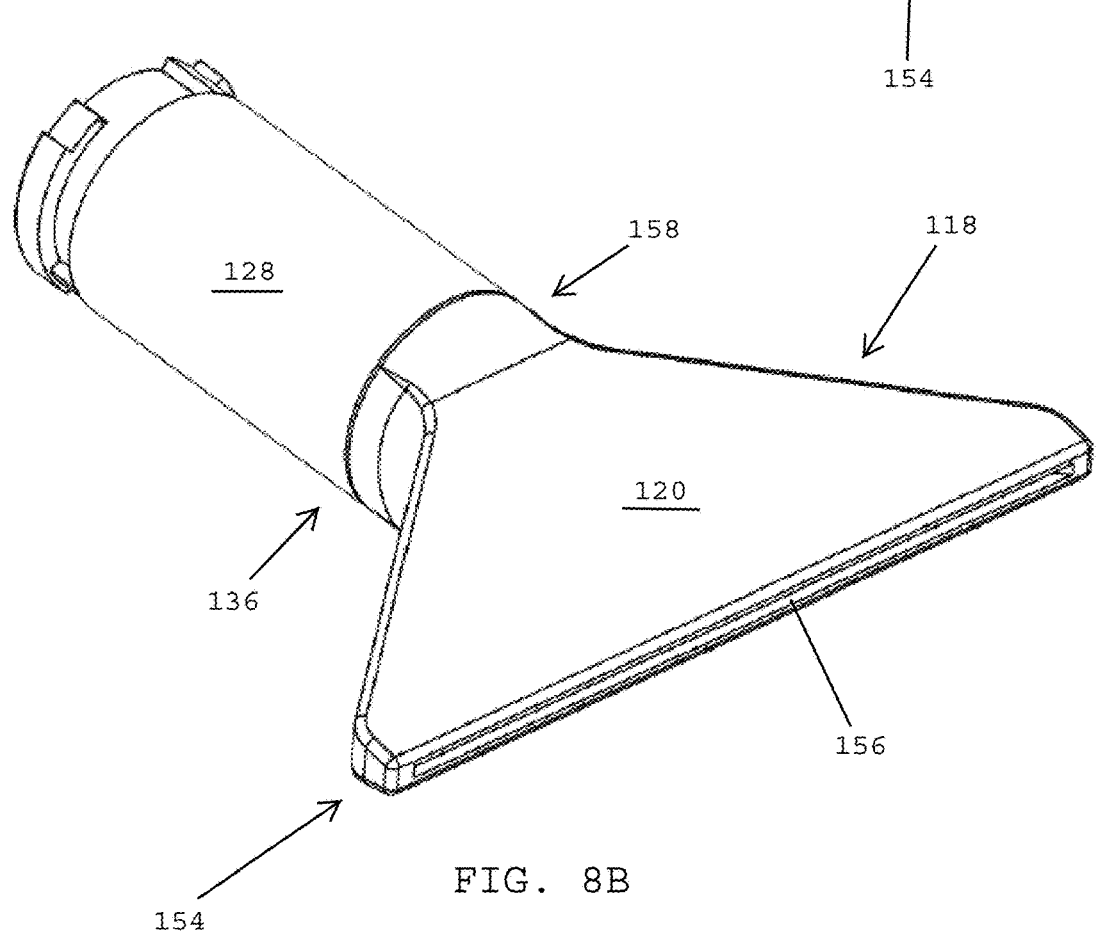
FIG. 8B is a perspective view of the flexible spreader and the static mixing tube of FIG. 8A.

Referring to FIGS. 8A and 8B, in one embodiment, the proximal end 150 of the flexible spreader 118 is preferably connected with the distal end 136 of the static mixing tube 128 so that after a composition is mixed within the static mixing tube 128 it may be directed from the distal end 136 of the static mixing tube 128 into the proximal opening at the proximal end 150 of the flexible spreader 118 for dispensing the curable composition from the elongated, flat dispensing opening 156 located at the distal end 154 of the flexible spreader 118. The outer surfaces of the flexible blade 120 may be used to spread the curable composition over a surface. A hot gas stream generated by the hot gas blower 122 (FIG. 1) may be directed onto the curable composition that is spread on the surface for rapidly curing (e.g., one minute cure time) the curable composition on the surface.

Figure 9:
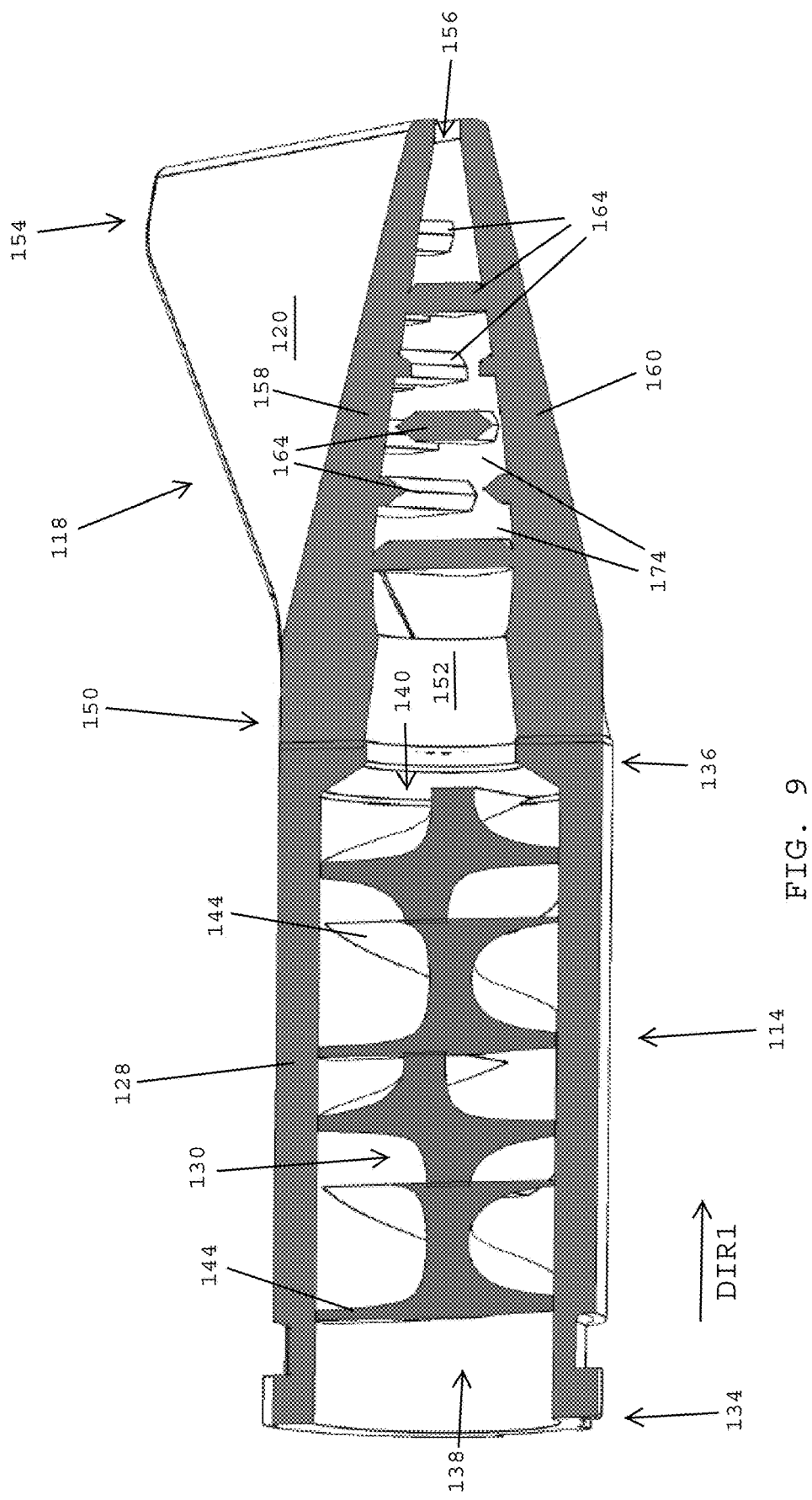
FIG. 9 is a cross-sectional view of the flexible spreader and the static mixing tube of FIGS. 8A and 8B.

Referring to FIG. 9, in one embodiment, the proximal end 150 of the flexible spreader 118 is connected with the distal end 136 of the static mixing tube 128 of the static mixer 114 (FIG. 1). In one embodiment, the two components that are expelled from the distal end of the double barrel syringe 102 (FIG. 1) are directed into the proximal opening 138 located at the proximal end 134 of the static mixing tube 128. The two components are forced to flow in the distal direction DIR1 for being advanced through the helical blades 144 of the helical baffle 130, which mixes the two components together to form a curable composition, such as a silicone-based, high viscosity curable composition that may be used as a topical skin adhesive (TSA) or a wound closure adhesive. After the two components are mixed together to form the curable composition, the composition is preferably dispensed from the distal opening 140 located at the distal end 136 of the static mixing tube 128 for being directed into the proximal opening 152 located at the proximal end 150 of the flexible spreader 118. Upon entering the flexible blade 120, the curable composition flows toward the distal end 154 of the flexible spreader 118. As the curable composition flows from the proximal end 150 to the distal end 154 of the flexible blade 120 of the flexible spreader 118, the curable composition travels through the tortuous pathways of the narrow channels 174 that are located between the spaced posts 164 that extend from the first wall 158 to the second wall 160 of the flexible blade 120. As the curable composition flows in the distal direction DIR1 through the tortuous pathway of the narrow channels 174, any air or gas bubbles that are present in the curable composition are preferably eliminated and/or dissipated, which will enhance the strength and structural integrity of a cured composition. The curable composition is preferably dispensed through the elongated, flat dispensing opening 156 that is located at the distal end 154 of the flexible blade 120 of the flexible spreader 118 for being applied onto a surface (e.g., a skin surface, tissue, a wound).

Figure 10A:
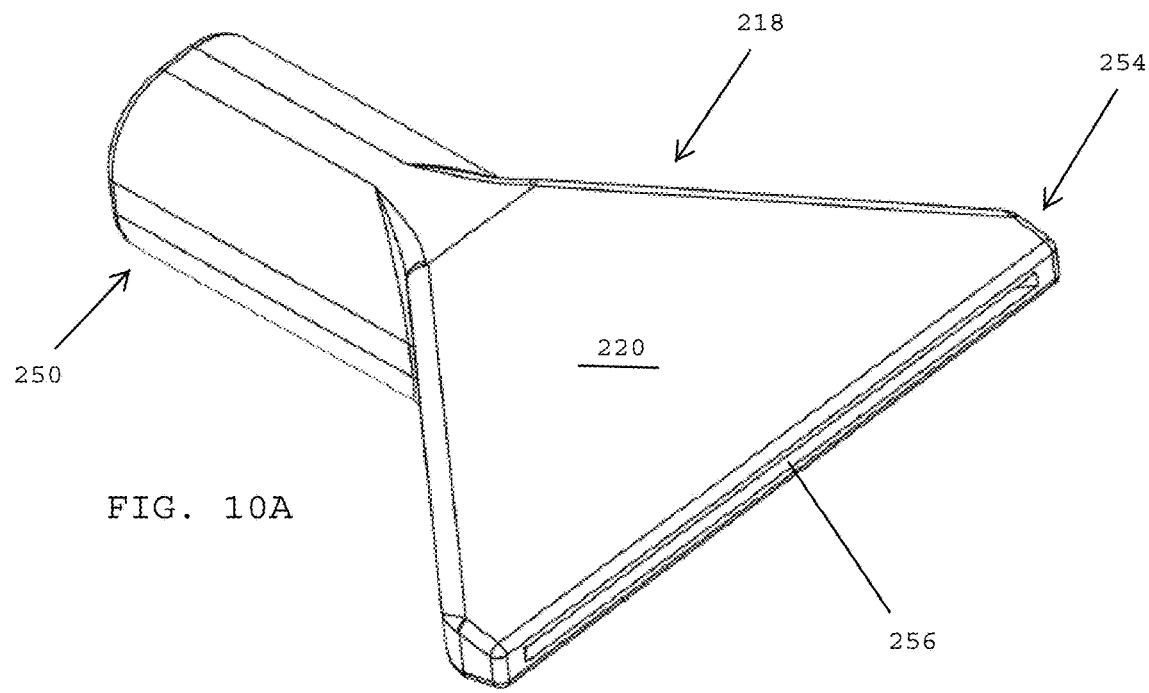
FIG. 10A is a perspective view of a distal end of a flexible spreader, in accordance with another embodiment of the present patent application.
Figure 10B:
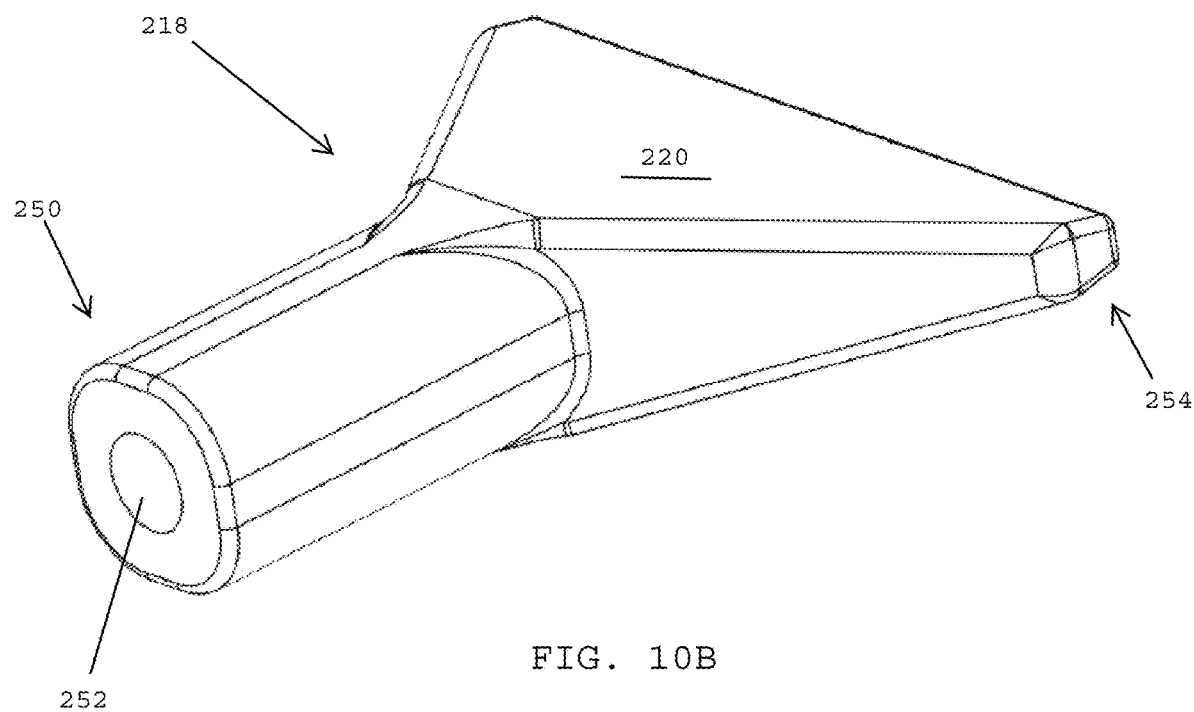
FIG. 10B is a perspective view of a proximal end of the flexible spreader shown in FIG. 10A.
Figure 10C:
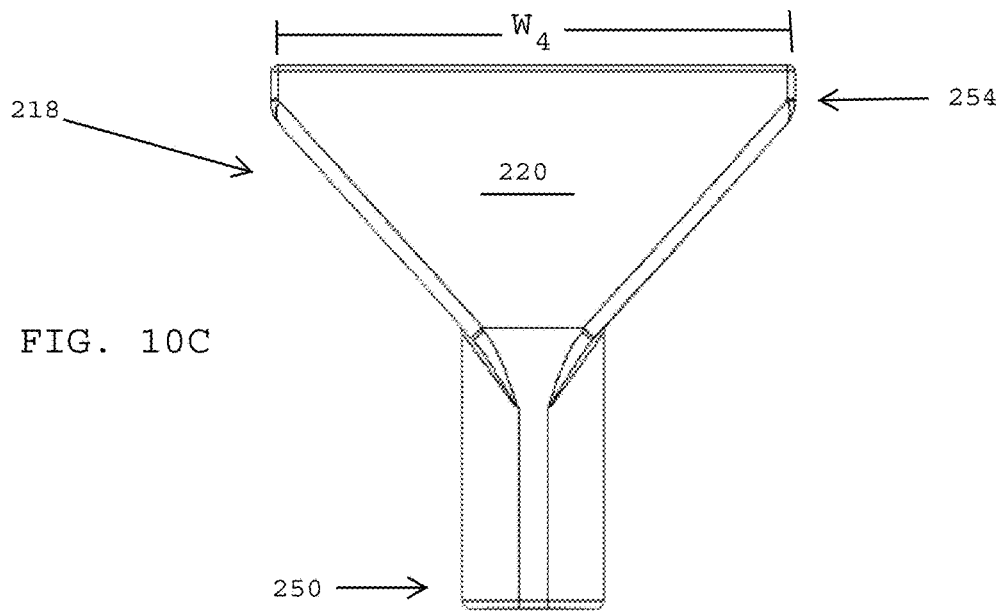
FIG. 10C is a top plan view of the flexible spreader shown in FIGS. 10A and 10B.

Referring to FIGS. 10A and 10B, in another embodiment, a flexible spreader 218 preferably includes a flexible blade 220 that is adapted to spread a curable composition that is dispensed from the flexible spreader. In one embodiment, the flexible spreader 218 preferably has a proximal end 250 including a proximal opening 252 and a distal end 254. In one embodiment, the proximal end 250 of the flexible spreader 218 is adapted to be secured to a distal end of a static mixer 114 (FIG. 1).

In one embodiment, the distal end of the flexible blade 220 preferably includes an elongated, flat dispensing opening 256 that extends across the width of the flexible blade 220 at the distal end of the flexible blade. In one embodiment, after the first and second components of a high viscosity curable composition have been mixed together within the static mixing tube of the static mixer 114 shown and described above in FIGS. 1, 3A-3E, 4A-4B, and 5, the curable composition may be directed into the proximal opening 252 at the proximal end 250 of the flexible spreader 218 for being dispensed from the elongated, flat dispensing opening 256 located at the distal end 254 of the flexible blade 220.

Referring to FIG. 10O, in one embodiment, the flexible spreader 218 preferably includes the flexible blade 220 that tapers outwardly (i.e., laterally) between the proximal end 250 and the distal end 254 of the flexible spreader 218. In one embodiment, the flexible blade 220 has a first width $W_3$ located at the proximal end of the flexible blade 220 and a second width $W_4$ located at the distal end of the flexible blade 220, which is greater than the first width $W_3$. In one embodiment, the flexible blade 220 may have a shape that is similar to that of a spatula for facilitating spreading a curable composition.

Figure 10D:
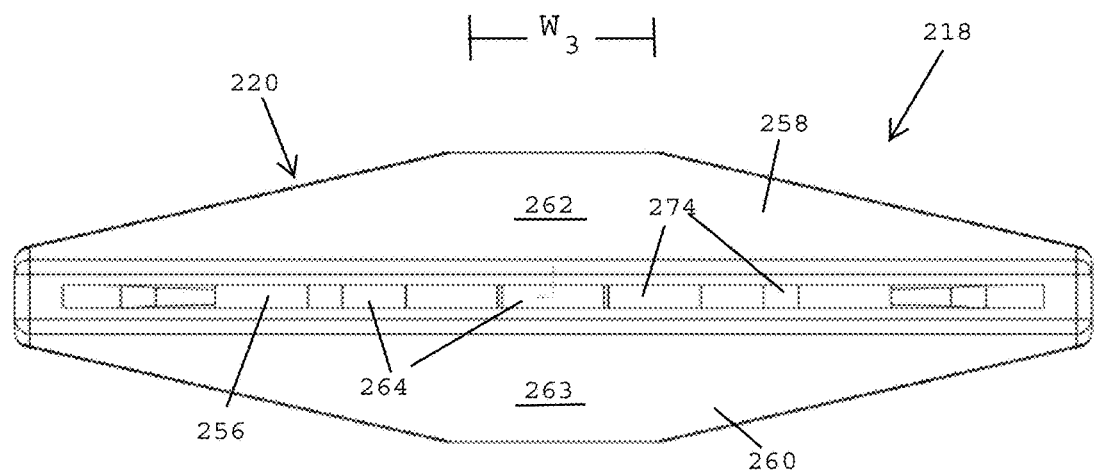
FIG. 10D is a distal end view of the flexible spreader shown in FIGS. 10A-10C.

Referring to FIG. 10D, in one embodiment, the distal end of the flexible blade 220 preferably includes the elongated, flat dispensing opening 256 that is adapted to dispense the curable composition from the distal end 254 of the flexible spreader 218. In one embodiment, the flexible blade 220 of the flexible spreader 218 preferably includes a first wall 258 that defines a first end (e.g., an upper end) of a flow channel for the curable composition that flows through the flexible blade, and a second wall 260 that defines a second end (e.g., a lower end) of the flow channel for the curable composition that flows through the flexible blade. The first and second walls 258, 260 are preferably spaced from one another to define the flow path for the curable composition that flows through the flexible blade 220 of the flexible spreader 218. In one embodiment, as the curable composition flows from the proximal end to the distal end of the flexible blade 220, the curable composition flows between the first wall 258 and the second wall 260, and around spaced posts 264, for being directed toward the elongated, flat dispensing opening 256 located at the distal end of the flexible blade 220.

In one embodiment, the first wall 258 of the flexible blade 220 preferably has a first major surface 262 (e.g., an outer surface) and the second wall 260 of the flexible blade 220 preferably has a second major surface 263 (e.g., an outer surface), whereby the first and second major surfaces 262, 263 may be used for spreading the curable composition that is dispensed from the elongated, flat dispensing opening 256.

In one embodiment, the flexible spreader 218 includes a plurality of the spaced posts 264 that extend from an inner surface of the first wall 258 to an opposing, inner surface of the second wall 260. The posts 264 preferably span the space or gap that is present between the first wall 258 and the second wall 260 to form a plurality of different, distinct flow channels 274 between the proximal and distal ends of the flexible spreader 218. The flow channels preferably define a plurality of tortuous pathways for the curable composition as it flows through the flexible spreader, which are adapted to breakup and/or eliminate any air or gas bubbles that are present in the curable composition before the curable composition is dispensed from the elongated, flat dispensing opening 256, which is located at the distal end 254 of the flexible blade 220 of the flexible spreader 218.

Figure 10E:
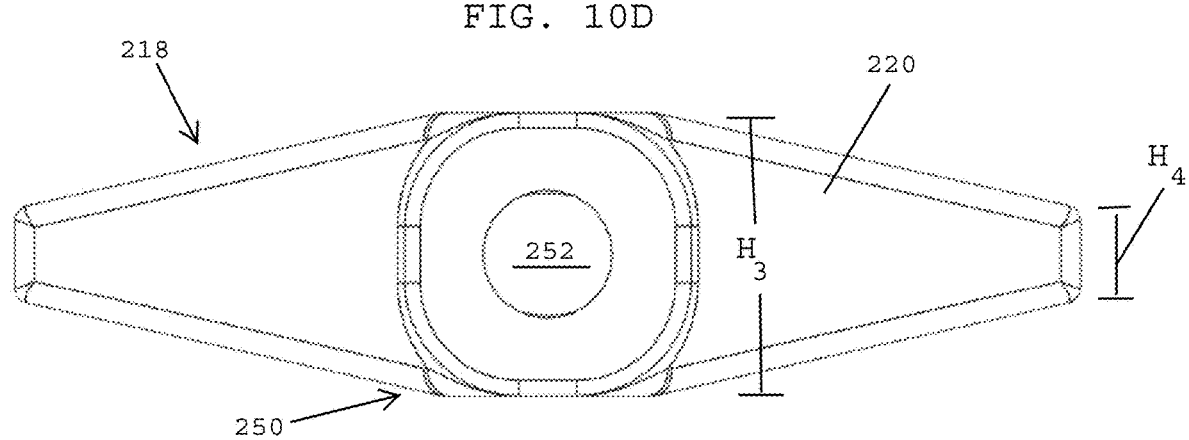
FIG. 10E is a proximal end view of the flexible spreader shown in FIGS. 10A-10D.

Referring to FIG. 10E, in one embodiment, the proximal end 250 of the flexible spreader 218 preferably includes the proximal opening 252 that is adapted to be coupled with the distal end of the static mixer 114 (FIG. 1) to receive the curable composition that is dispensed from the distal end of the static mixing tube 228 (FIG. 5) of the static mixer 114. In one embodiment, the flexible blade 220 may be thicker at a central region thereof and thinner at outer or lateral regions thereof. In one embodiment, the central region of the flexible blade 220 preferably has a first height $H_3$ that is greater than the second $H_4$ of the flexible blade 220 at outer or lateral ends of the flexible blade.

Figure 10F:
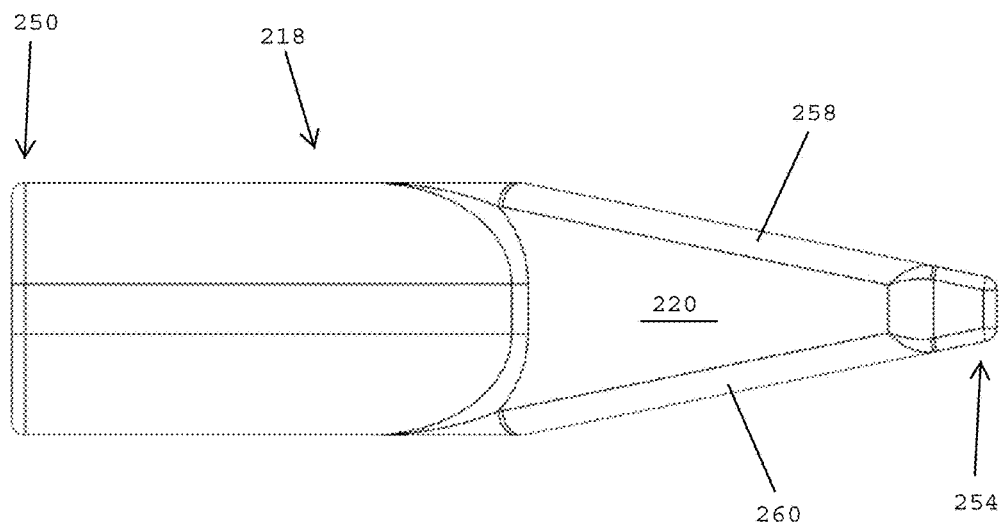
FIG. 10F is a side elevation view of the flexible spreader shown in FIGS. 10A-10E.
Figure 10G:
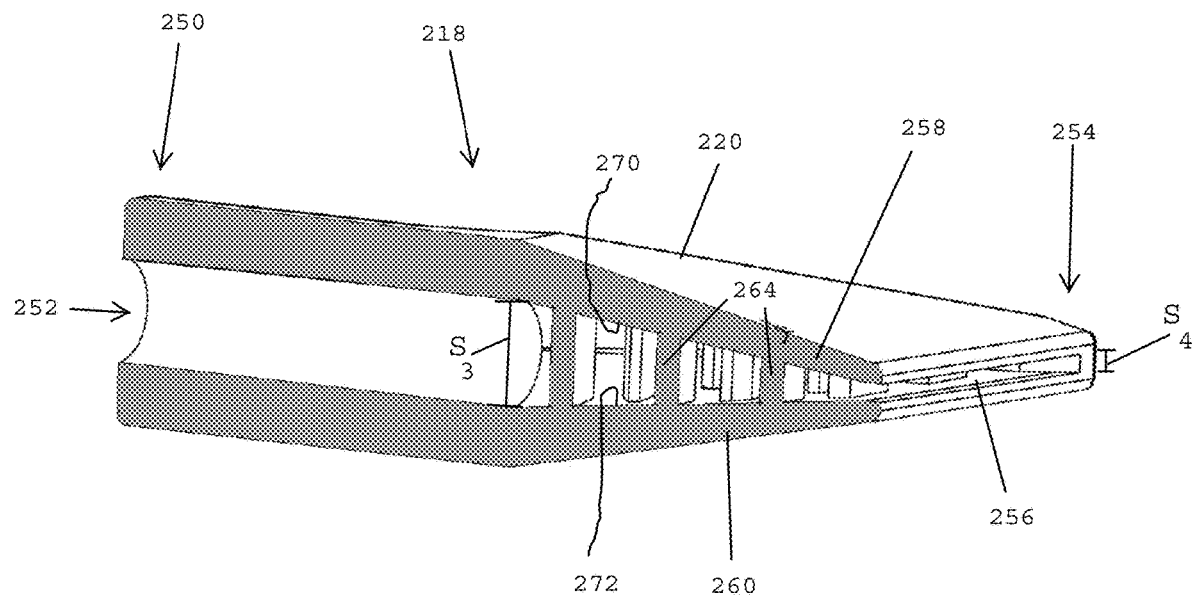
FIG. 10G is a cross-sectional view of the flexible spreader shown in FIGS. 10A-10F.

Referring to FIGS. 10F and 10G, in one embodiment, the flexible spreader 218 preferably includes the proximal end 250 having the proximal opening 252 and the distal end 254 having the elongated, flat dispensing opening 256. The flexible spreader 218 desirably includes the flexible blade 220 having the first wall 258 that is spaced away from the second wall 260 so that the curable composition that is directed into the proximal opening 252 may flow between an inner surface 270 of the first wall 258 and an opposing inner surface 272 of the second wall 260 for being dispensed from the elongated, flat dispensing opening 256 that is located at the distal end 254 of the flexible spreader 218.

In one embodiment, the first and second walls 258, 260 of the flexible blade 220 preferably taper inwardly toward one another from the proximal end 250 of the flexible spreader 218 to the distal end 254 of the flexible spreader 218. As a result, the flexible blade may be thicker at a proximal end thereof and thinner at a distal end thereof, whereby the spacing $S_3$ between proximal ends of the first and second walls 258, 260 (i.e., at the proximal end of the flexible blade 220) is greater than the spacing $S_4$ between distal ends of the first and second walls 258, 260 (i.e., at the distal end of the flexible blade 220).

Referring to FIG. 10G, in one embodiment, the flexible spreader 218 preferably includes a plurality of spaced posts 264 that extend from the first wall 258 to the second wall 260 of the flexible blade 220 to form a plurality of narrow flow channels 274 that extend between the posts 264 for breaking up any air or gas bubbles that may be present in the curable composition as the curable composition flows distally from the proximal end 250 to the distal end 254 of the flexible blade 220 of the flexible spreader 218.

Figure 11A:
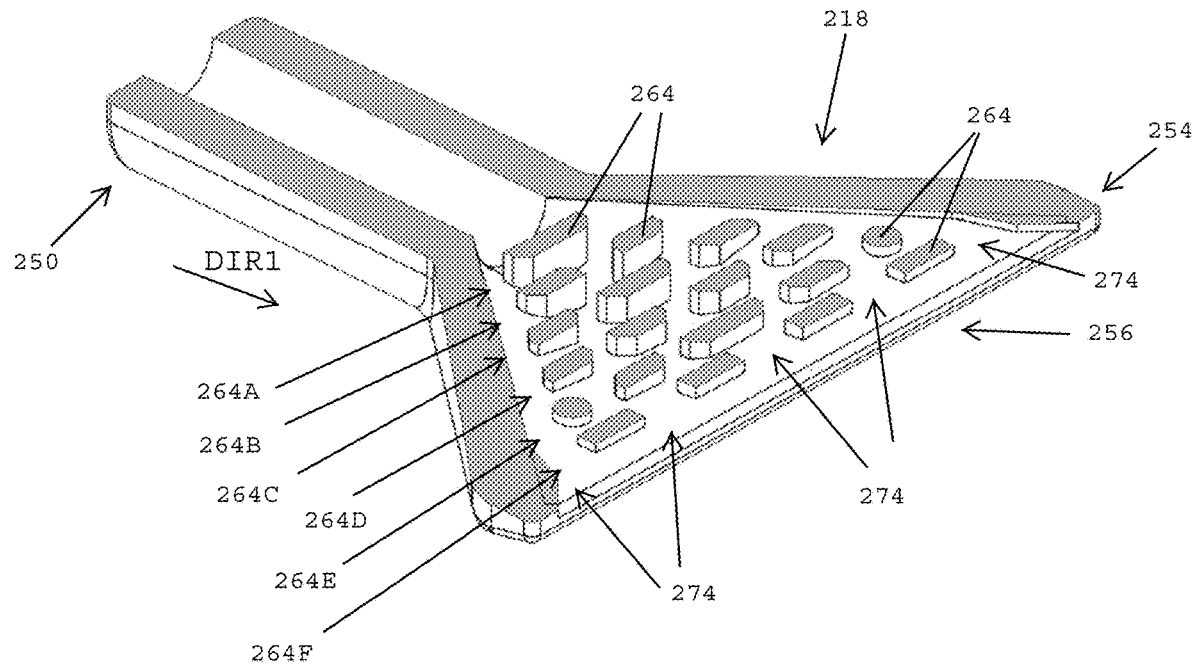
FIG. 11A is another cross-sectional view of the flexible spreader shown in FIGS. 10A-10F.
Figure 11B:
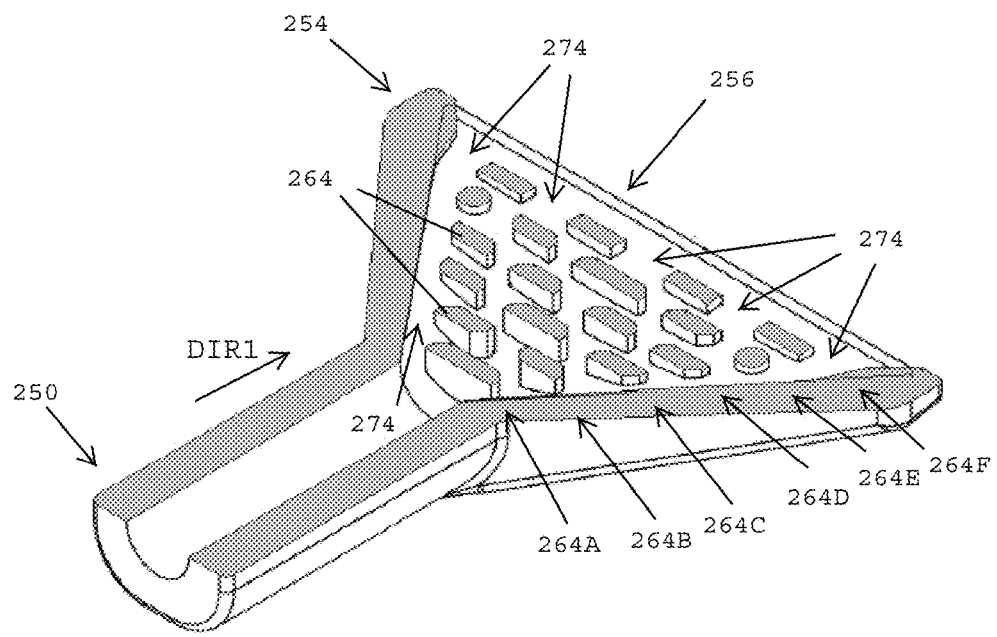
FIG. 11B is yet another cross-sectional view of the flexible spreader shown in FIGS. 10A-10F and FIG. 11A.

Referring to FIGS. 11A and 11B, in one embodiment, the flexible spreader 218 preferably includes the plurality of posts 264 that are spaced from one another between the proximal end 250 and the distal end 254 of the flexible spreader 218. In one embodiment, the plurality of posts 264 are spaced from one another for defining the plurality of narrow flow channels 274 that are located between the spaced posts 264. The narrow flow channels 274 define tortuous flow paths for the curable composition as it flows in the distal direction DIR1 for being dispensed through the elongated, flat dispensing opening 256 (FIG. 10A) located at the distal end 254 of the flexible spreader 218.

In one embodiment, the spaced posts 264 may be divided into rows of posts 264A-264F, whereby the posts in any one row have heights that are greater (i.e., taller) in the center of the flexible blade 220 and smaller (i.e., shorter) in the lateral regions of the flexible blade 220. In one embodiment, the posts 264 within a row may become progressively shorter when moving from a central region of the row to the outer, lateral regions of the row.

In one embodiment, one of the parts of the two part silicone based topical skin adhesive may include a catalyst for precipitating a chemical reaction between the two parts of the silicone adhesive.

Karstedt of GE Silicone invented a highly active platinum catalyst at the beginning of the 1970's, which was disclosed in U.S. Pat. No. 3,775,452. Vinyl terminated polydimethylsiloxane can react with polymethylhydrosiloxane containing cross linker in less than 1 minute at ambient temperature with as little as 10 ppm of the Karstedt catalyst. The traditional platinum catalyst does not enable the reaction between OH groups on the surface of silica particles reacts and the OH functions on the surface of substrate. This type of condensation reaction tends to be slow at ambient condition and the typical catalyst for this reaction including organic amine and catalyst such as tin dilaurate. Trace amount of condensation catalyst will terminate the catalytic ability of platinum catalyst which is referred as platinum poisoning in the silicone industry. A novel platinum comparable catalyst is needed to activate the OH condensation between silica particle and substrate material, to enable rapid adhesion formation between silicone and a given substrate material. A platinum based novel catalyst of the present invention is able to activate both vinyl silylation and OH condensation simultaneously.

The novel catalyst disclosed in the present patent application is prepared by reacting Karstedt's catalyst with diethyl maleate according to Scheme 1. The novel platinum tetramethyldivinyl disiloxane diethyl maleate catalyst enables both vinyl silylation and a condensation reaction. This is referred to as a "dual functional silicone catalyst".

Scheme 1

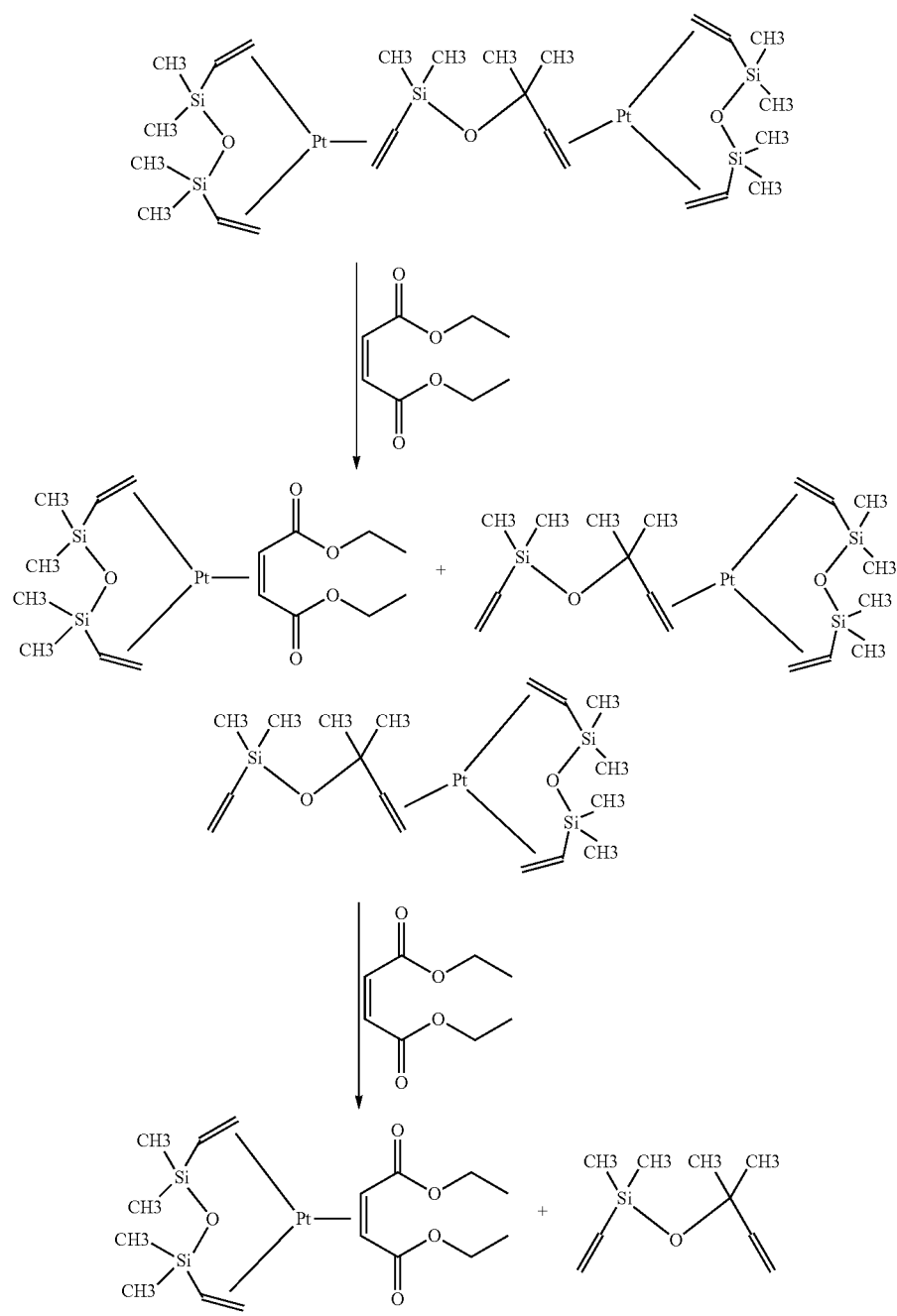

The novel catalyst disclosed in the present patent application may be prepared in the following manner: a Karstedt catalyst in xylene solution is mixed with diethyl maleate at ambient temperature for a sufficiently effective time to complete the reaction, e.g., 10 hours.

The resulting catalyst solution containing the novel catalyst of the present patent application is ready to use in a composition useful as a topical skin adhesive. The formula of the resulting platinum complex catalyst (platinum tetramethyldivinyl disiloxane diethyl maleate complex) is:

$$Pt[(CH_2=CH)(CH_3)_2Si]_2O\cdot(COOH=CHCO)(C_2H_5O)_2.$$

It should be noted that the resulting catalyst reaction mixture will contain a small amount of the reaction product divinyltetramethyldisiloxane. This component does not affect the catalyst and is a low boiling point component that is rapidly evaporated. Accordingly, purification of the catalyst mixture to remove divinyltetramethyldisiloxane is optional, and it is believed that its presence at ultra low concentrations will not affect the cross-linking reaction of a cross-linkable silicone polymer. The novel catalyst of the present invention also actives the bonding formation between silanol groups on the surface of silica fillers and OH functions on a given surface, that is, the catalyst is capable to activate two reactions. This allows for curing the cross-linkable components in silicone coatings to rapidly form coating films at desired curing temperatures and provides bonding to a given substrate such as human skin.

In one embodiment, a curable composition may include a catalyst, which may be formulated as set forth in Example 1 of the present patent application.

EXAMPLE 1

Novel Platinum Catalyst (Synthesis Procedure)

44.50 g of Gelest SIP 6831.2 (2.2% platinum divinyl tetramethyldisiloxane complex in xylene, Karstedt catalyst) was mixed with 2 g of diethyl maleate for 24 hours at ambient temperature. Samples were taken out after 3 hours, 18 hours, and 24 hours for NMR testing and the NMR spectra for the 3 hour sample is shown in FIG. 12.

The formation of the novel catalyst is the evidence for scheme 1, which rests on NMR spectroscopic identification. Karstedt catalyst is known with a characteristic $^{195}$Pt signal at approximately −6111 ppm.

Figure 12:
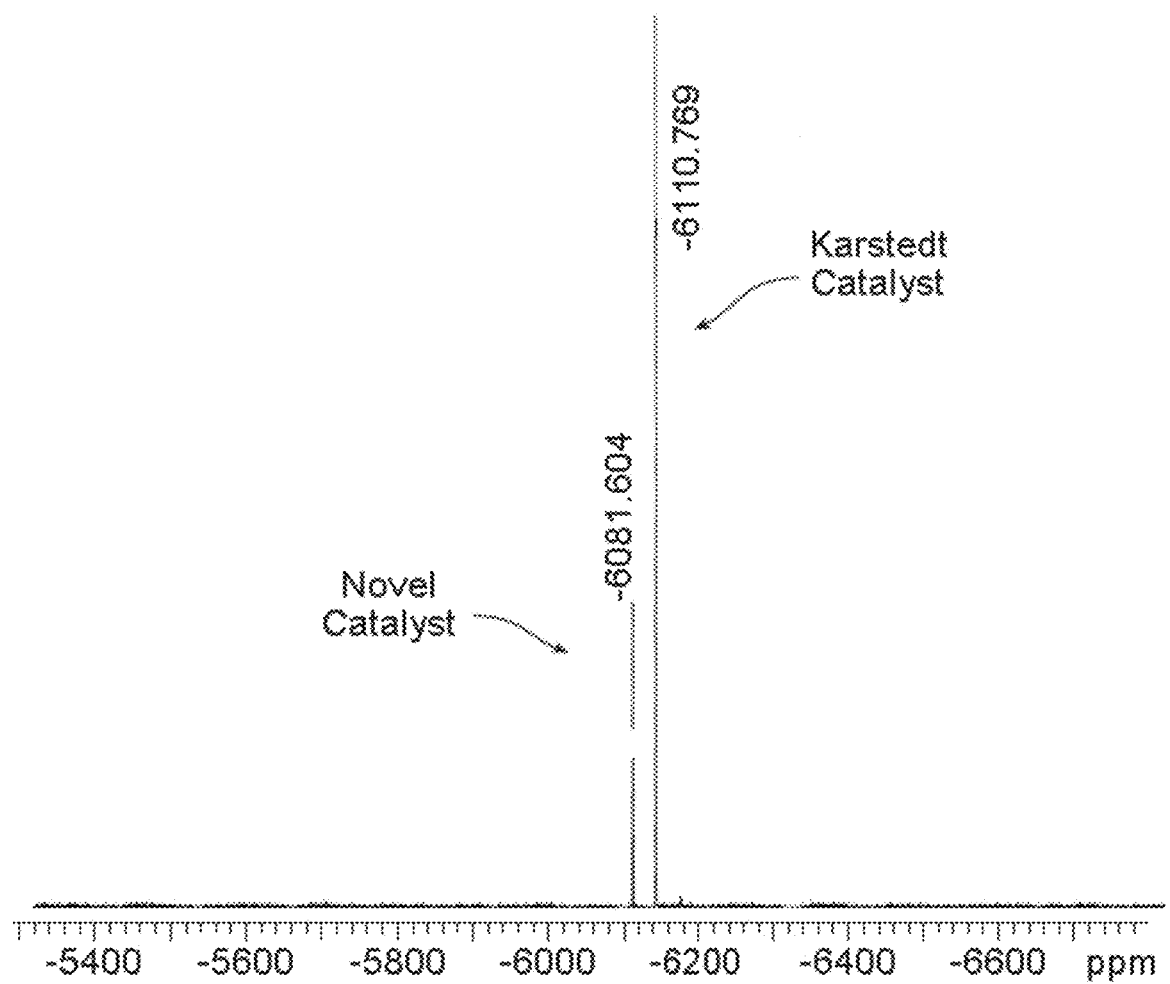
FIG. 12 is an NMR peak comparison of the Karstedt Catalyst compared with the NMR peak of the novel catalyst of this invention.

After 3 hours of mixing of the mixtures of Example 1, a new $^{195}$Pt signal at −6082 ppm was observed along with the original signal for the Karstedt catalyst at −6111 ppm as illustrated in the NMR spectra of this mixture at 3 hours in FIG. 12. The intensity of the new signal increases over time while the intensity of the Karstedt catalyst signal reduced at the same time.

In one embodiment, the curable composition may include silicone-based topical skin adhesives, which are formulated as set forth below in Examples 2 and 3 of the present patent application.

EXAMPLE 2

Preparation of Silicone-Based Topical Skin Adhesive

In general and similar to most of commercially available platinum cured silicone materials, the silicone-based topical skin adhesive is delivered in a two-part kit by mixing equal volumes of the Part A and Part B components.

As an overview, vinyl terminated polydimethylsiloxane is mixed with Platinum tetramethyldivinyl disiloxane diethyl maleate catalyst, silica particles and optionally aliphatic organic solvent using a high-speed mixer to form part A of the kit. Vinyl terminated polydimethylsiloxane were mixed with polymethylhydro-co-polydimethylsiloxane cross linker, silica particle and optionally aliphatic organic solvent using high speed mixer to form part B of the kit.

Equal amounts of the two-part kit were mixed using a static mixer and then spread onto the surface of a substrate, such as skin. The mixture of the two-part kit cured within 5 minutes at body temperature as determined by the loss of stickiness or tackiness of the applied silicone.

Part A. 40 g of vinyl terminated polydimethylsiloxane (Gelest DMSV41) was mixed with 10 g of surface treated silica particles (Gelest SIS6962.0), together with 2.6 g of the resulting catalyst of Example 1 using a high-speed centrifugal mixer (FlackTek DAC150 FV-K) at 3470 rpm for 5 minutes.

Part B. 40 g of vinyl terminated polydimethylsiloxane (Gelest DMSV41) was mixed with 10 g of surface treated silica particles (Gelest SIS6962.0), together with 3.34 g of Polymethylhydro-co-polydimethylsiloxane (Gelest HMS301) using a high-speed centrifugal mixer (FlackTek DAC150 FV-K) at 3470 rpm for 5 minutes.

EXAMPLE 3

Preparation of Silicone-Based Topical Skin Adhesive Using Commercial Silica-Containing Silicone Raw Material Part A. 90 g of Elkem 44 experimental base (containing vinyl terminated polydimethyl silicone base polymer and fume silica particles) was mixed with 4.72 g of the resulting catalyst of Example 1, 9.0 g of low molecular weight vinyl terminated polydimethyl silicone base polymer (Gelest DMS V21) and 26 g of hexane using a high-speed centrifugal mixer (FlackTek DAC150 FV-K) at 3470 rpm for 5 minutes.

Part B. 81 g of Elkem 44 experimental base (containing vinyl terminated polydimethyl silicone base polymer and fume silica particles) was mixed with 8.1 g of polymethyl hydro siloxane cross linker (Gelest DMS H991), 2.7 g of SiH terminated polydimethylsiloxane chain extender (Gelest DMS H21) and 10.2 g of hexane using a high speed centrifugal mixer (FlackTek DAC150 FV-K) at 3470 rpm for 5 minutes.

Control Example: Control Example Without Silica Bonding Agent and Using Conventional Karstedt Catalyst Part A. 40 g of vinyl terminated polydimethylsiloxane (Gelest DMSV41) was mixed with 2.6 g of Karstedt catalyst xylene solution (1% of Gelest SIP 6831.2 in xylene) using a high-speed centrifugal mixer (FlackTek DAC150 FV-K) at 3470 rpm for 5 minutes.

Part B. 40 g of vinyl terminated polydimethylsiloxane (Gelest DMSV41) was mixed 3.34 g of Polymethylhydro-co-polydimethylsiloxane (Gelest HMS301) using a high-speed centrifugal mixer (FlackTek DAC150 FV-K) at 3470 rpm for 5 minutes.

As noted above and as would be appreciated by one of skill in the art, the silicone compositions disclosed in the present patent application cure in several minutes to films that are neither sticky nor tacky. In contrast, some silicone adhesives, such as silicone pressure sensitive adhesives (PSA's), are by nature sticky or tacky and are intended to be such for the entire usable life of the adhesive. Such useable life of the tacky silicone PSA's may be upwards to several years. The non-tackiness of the compositions and examples of this invention is measured by ASTM 0679.

In general ASTM C679 consists of lightly touching a surface of a curing sealant with a polyethylene film at regular intervals until the sealant does not attach itself to the film and the film appears clean when peel from the surface. More specifically a strip of polyethylene film is placed on the surface of the curing elastomer and a 30 g weight is placed on the film. The weight is left in place for 30 seconds, then removed and the polyethylene strip is removed and examined for sealant attachment to the film. The length of time from when the sealant was first applied onto a given surface until the time the sealant is no longer picked up by the film is called tack-free time and is the time point at which the film exhibits a non-tacky nature which evidences that the sealant has cured.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for dispensing a curable composition comprising:
a delivery device;
a static mixer having a proximal end that is connected with a distal end of said delivery device; and
a flexible spreader having a proximal end that is connected with a distal end of said static mixer, a distal end including a flat dispensing opening, and a plurality of channels extending through said flexible spreader to said flat dispensing opening, wherein said flexible spreader includes a flexible blade having a proximal end and a distal end, said flexible blade comprising:
a first wall extending from the proximal end to the distal end of said flexible blade; and
a second wall extending from the proximal end to the distal end of said flexible blade;
said plurality of channels extending between said first and second walls to said flat dispensing opening at the distal end of said flexible spreader, wherein said flexible spreader further comprises a plurality of spaced posts extending from said first wall to said second wall for defining said plurality of channels.

2. The system as claimed in claim 1, further comprising a hot gas blower configured to generate a hot gas stream that flows distally over the distal end of said flexible spreader.

3. The system as claimed in claim 1, wherein said delivery device contains at least one component of a curable composition, and wherein said delivery device is configured to expel said at least one component from said delivery device into the proximal end of said static mixer.

4. The system as claimed in claim 3, wherein said delivery device includes a dual barrel syringe comprising:
a first syringe barrel containing a first component of said curable composition and a first plunger disposed within said first syringe barrel;
a second syringe barrel containing a second component of said curable composition and a second plunger disposed within said second syringe barrel, wherein said first and second plungers are moveable toward distal ends of said respective first and second syringe barrels for expelling said first and second components from the distal ends of said respective first and second syringe barrels and into the proximal end of said static mixer.

5. The system as claimed in claim 4, further comprising a tab interconnecting proximal ends of said first and second plungers for simultaneously moving said first and second plungers toward the distal ends of said respective first and second syringe barrels for expelling said first and second components.

6. The system as claimed in claim 3, wherein said curable composition is selected from the group consisting of polyurethane, acrylic, methyl methacrylate, silicone, condensation cured silicone, epoxy, polysulfide, and high viscosity curable biocompatible compositions having viscosities greater than 5000 cps.

7. The system as claimed in claim 3, wherein said curable composition comprises:
a cross-linkable silicone polymer having reactive functionalities;
a silica-containing composition;
a silicone cross-linking agent; and,
a catalyst, wherein said catalyst comprises a platinum tetramethyldivinyl disilosane diethyl maleate complex having the formula:

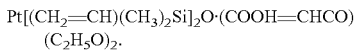

8. The system as claimed in claim 7, wherein the cross-linkable silicone polymer is selected from the group consisting of vinyl terminated polydialkylsiloxane, vinyl terminated polydimethylsiloxane, vinyl terminated polydiphenylsilane-dimethylsiloxane copolymer, vinyl terminated polyphenylmethylsiloxane, vinyl terminated polyfluoropropylmethyl-dimethylsiloxane copolymer, vinyl terminated polydiethylsiloxane, and SiH terminated polydimethyldisiloxane.

9. The system as claimed in claim 1, wherein said static mixer comprises:
a static mixing tube having a proximal end with a proximal opening, a distal end with a distal opening, and a conduit that extends from the proximal opening to the distal opening;
at least one helical baffle disposed within the conduit of said static mixing tube, wherein said at least one helical baffle includes helically wounds blades adapted to mix said first and second components together to form said curable composition as said first and second components flow from the proximal end to the distal end of said static mixing tube.

10. The system as claimed in claim 1, wherein said flexible blade is made of a material selected from the group consisting of silicones, rubbers, and polymers having a 0-80 durometer Shore A hardness rating.

11. The system as claimed in claim 1, wherein said first wall has an inner surface and said second wall has an inner surface that opposes said inner surface of said first wall, wherein said spaced posts extend from said inner surface of said first wall to said inner surface of said second wall.

12. The system as claimed in claim 1, wherein the distance between the proximal ends of said first and second walls of said flexible blade is greater than the distance between the distal ends of said first and second walls of said flexible blade.

13. The system as claimed in claim 1, wherein said flexible blade has a first width at the proximal end thereof and a second width at the distal end thereof that is greater than the first width so that the distal end of said flexible blade is wider than the proximal end of said flexible blade.

14. A system for dispensing a curable composition comprising:
a dual barrel syringe including
a first syringe barrel containing a first component of a curable composition and a first plunger disposed within said first syringe barrel, and
a second syringe barrel containing a second component of said curable composition and a second plunger disposed within said second syringe barrel;
a static mixer having a proximal end that is connected with distal ends of said respective first and second syringe barrels, wherein said first and second plungers are moveable toward the distal ends of said respective first and second syringe barrels for expelling said first and second components from the distal ends of said respective first and second syringe barrels into the proximal end of said static mixer for mixing said first and second components to form said curable composition;

a flexible spreader having a proximal end that is connected with a distal end of said static mixer, a distal end including a flat dispensing opening, and a plurality of channels extending to said flat dispensing opening that are configured to deliver said curable composition from said static mixer to said flat dispensing opening; and a hot gas blower configured to generate a hot gas stream that flows distally over the distal end of said flexible spreader for curing said curable composition dispensed from said flat dispensing opening, wherein said flexible spreader includes a flexible blade having a proximal end and a distal end, said flexible blade comprising:

a first wall extending from the proximal end to the distal end of said flexible blade;

a second wall extending from the proximal end to the distal end of said flexible blade; and a plurality of spaced posts extending from said first wall to said second wall for defining said plurality of channels extending between said first and second walls to said flat dispensing opening at the distal end of said flexible spreader.

15. The system as claimed in claim 14, wherein the distance between the proximal ends of said first and second walls of said flexible blade is greater than the distance between the distal ends of said first and second walls of said flexible blade, and wherein said flexible blade has a first width at the proximal end thereof and a second width at the distal end thereof that is greater than the first width so that the distal end of said flexible blade is wider than the proximal end of said flexible blade.

16. A system for dispensing a curable composition comprising:

a dual barrel syringe including a first syringe barrel containing a first component of a curable composition and a first plunger disposed within said first syringe barrel, a second syringe barrel containing a second component of said curable composition and a second plunger disposed within said second syringe barrel;

a static mixer having a proximal end that is connected with distal ends of said respective first and second syringe barrels, wherein said first and second plungers are moveable toward the distal ends of said respective first and second syringe barrels for expelling said first and second components from the distal ends of said respective first and second syringe barrels into the proximal end of said static mixer for mixing said first and second components to form said curable composition;

a flexible spreader having a proximal end that is connected with a distal end of said static mixer, a distal end including a flat dispensing opening, and a plurality of channels extending to said flat dispensing opening that are configured to deliver said curable composition from said static mixer to said flat dispensing opening; and a hot gas blower configured to generate a hot gas stream that flows distally over the distal end of said flexible spreader for curing said curable composition dispensed from said flat dispensing opening, wherein said spaced posts are arrayed in a matrix pattern, and wherein said plurality of channels extend between said spaced posts to define tortuous flow paths for said curable composition flowing through said flexible blade to said flat dispensing opening.

17. The system as claimed in claim 14, wherein said flexible spreader is made of a material selected from the group consisting of silicones, rubbers, and polymers having a 0-80 durometer Shore A hardness rating.

* * * * *